US009580492B2

(12) United States Patent
Chen et al.

(10) Patent No.: US 9,580,492 B2
(45) Date of Patent: *Feb. 28, 2017

(54) MONOCLONAL ANTIBODIES THAT NEUTRALIZE ANTHRAX TOXINS

(71) Applicant: The United States of America, as represented by the Secretary, Dept. of Health and Human Services, Washington, DC (US)

(72) Inventors: Zhaochun Chen, North Potomac, MD (US); Robert H. Purcell, Gaithersburg, MD (US); Suzanne U. Emerson, Gaithersburg, MD (US); Stephen H. Leppla, Bethesda, MD (US); Mahtab Moayeri, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/595,475

(22) Filed: Jan. 13, 2015

(65) Prior Publication Data

US 2016/0200803 A1    Jul. 14, 2016

Related U.S. Application Data

(62) Division of application No. 14/031,508, filed on Sep. 19, 2013, now Pat. No. 8,961,975, which is a division of application No. 13/310,463, filed on Dec. 2, 2011, now Pat. No. 8,574,853, which is a division of application No. 12/528,427, filed as application No. PCT/US2008/054609 on Feb. 21, 2008, now Pat. No. 8,071,100.

(60) Provisional application No. 60/903,022, filed on Feb. 23, 2007.

(51) Int. Cl.

| G01N 33/573 | (2006.01) |
| C07K 16/12 | (2006.01) |
| C07K 16/40 | (2006.01) |
| A61K 51/10 | (2006.01) |
| G01N 33/569 | (2006.01) |
| A61K 39/00 | (2006.01) |

(52) U.S. Cl.
CPC ...... *C07K 16/1278* (2013.01); *A61K 51/1009* (2013.01); *C07K 16/40* (2013.01); *G01N 33/56911* (2013.01); *G01N 33/573* (2013.01); *A61K 2039/505* (2013.01); *C07K 2317/21* (2013.01); *C07K 2317/24* (2013.01); *C07K 2317/51* (2013.01); *C07K 2317/515* (2013.01); *C07K 2317/55* (2013.01); *C07K 2317/565* (2013.01); *C07K 2317/76* (2013.01); *C07K 2317/92* (2013.01); *G01N 2333/32* (2013.01); *G01N 2333/954* (2013.01); *G01N 2469/10* (2013.01)

(58) Field of Classification Search
None
See application file for complete search history.

(56) References Cited

FOREIGN PATENT DOCUMENTS

WO     WO 2005/120567     12/2005

OTHER PUBLICATIONS

Arora, N. et al., "Fusions of anthrax toxin lethal factor with shiga toxin and diphtheria toxin enzymatic domains are toxic to mammalian cells," Infect Immun., Nov. 1994, 62(11):4955-61.
Brossier, F. et al, "Infect Immun. Nov. 2004;72(11):6313-7," Infect Immun, Nov. 2004 72(11):6313-7.
Casset et al., "A peptide mimetic of an anti-CD4 monoclonal antibody by rational design," Biochemical and Biophysical Research Communications, 2003, vol. 307, pp. 198-205.
Chen et al., "Selection and Analysis of an Optimized Anti-VEGF Antibody: Crystal Structure of an Affinity-matured Fab in Complex with Antigen," J. Mol. Bio., 1999, vol. 293, pp. 865-881.
Chen, Z. et al, "Chimpanzee/human mAbs to vaccinia virus B5 protein neutralize vaccinia and smallpox viruses and protect mice against vaccinia virus," Proc Natl Aced Sci USA, Feb. 2006, 103(6):1882-7; Epub Jan. 25, 2006.
Chen, Z. et al., "Efficient neutralization of anthrax toxin by chimpanzee monoclonal antibodies against protective antigen," J Infect Dis., Mar. 2006, 193(5):625-33, Epub Feb. 2, 2006.
Chothia, et al., "The relation between the divergence of sequence and structure in proteins," The EMBO Journal, 1986, 5/4:823-26.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, 2002, vol. 169, pp. 3076-3084.
Galloway, D. et al., "Genetic immunization against anthrax," Vaccine, Apr. 2004, 22(13-14):1604-8.
Greenspan, et al., "Defining epitopes: It's not as easy as it seems," Nature Biotechnology, 1999, 7:936-937.
Holm et al., "Functional mapping and single chain construction of the anti-cytokeratin 8 monoclonal antibody TS1," Molecular Immunology, 2007, vol. 44, pp. 1075-1084.

(Continued)

*Primary Examiner* — Jennifer Graser
(74) *Attorney, Agent, or Firm* — Sheridan Ross P.C.

(57) ABSTRACT

The present invention relates to monoclonal antibodies that bind or neutralize anthrax lethal factor (LF), edema factor (EF), and/or protective antigen (PA). The invention provides such antibodies, fragments of such antibodies retaining anthrax toxin-binding ability, fully human or humanized antibodies retaining anthrax toxin-binding ability, and pharmaceutical compositions including such antibodies. The invention further provides for isolated nucleic acids encoding the antibodies of the invention and host cells transformed therewith. Additionally, the invention provides for prophylactic, therapeutic, and diagnostic methods employing the antibodies and nucleic acids of the invention.

9 Claims, 12 Drawing Sheets

(56) References Cited

OTHER PUBLICATIONS

Lim, Nam-Kyu, et al., "An Anthrax Lethal Factor-Neutralizing Monoclonal Antibody Protects Rats before and after Challenge with Anthrax Toxin," Infection and Immunity, vol. 73, No. 10, Oct. 1, 2005, pp. 6547-6551.

Little, F Stephen, "Structure-Function Analysis of *Bacillus anthracis* edema factor by using moriclonal antibodies," Biochemical and Biophysical Research Communications, vol. 199, No. 2, Mar. 15, 1994, pp. 676-682.

Little, S. F. et al., "Production and characterization of monoclonal antibodies to the protective antigen component of *Bacillus anthracis* toxin," Infect Immun, Jul. 1988, 56(7):1807-13.

Little, S.F., et al., "Production and Characterization of Monoclonal Antibodies against the Lethal Factor Component of *Bacillus anthracis* lethal toxin", Infection and Immunity, vol. 58, No. 6, Jun. 1990, pp. 1606-1613.

MacCallum et al., "Antibody-antigen Interactions: Contact Analysis and Binding Site Topography," J. Mol. Biol. (1996) 262,732-745.

Maynard, J. A. et al., "Protection against anthrax toxin by recombinant antibody fragments correlates with antigen affinity," Nat Biotechnol, Jun. 2002, 20(6):597-601.

Mikayama et al., "Molecular cloning and functional expression of a cDNA encoding glycosylation-inhibiting factor," (Nov. 1993. Proc.Natl.Acad.Sci. USA, vol. 90:10056-10060).

Milne, J. C. et al., "Protective antigen-binding domain of anthrax lethal factor mediates translocation of a heterologous protein fused to its amino- or carboxy-terminus," Mol Microbiol, Feb. 1995, 15(4):661-6.

Peterson, J. W. et al., "Human monoclonal antibody AVP-21D9 to protective antigen reduces dissemination of the *Bacillus anthracis* Ames strain from the lungs in a rabbit model," Infect Immun, Jul. 2007, 75(7):3414-24; Epub Apr 23, 2007.

Pezard, C. et al., "Protective immunity induced by *Bacillus anthracis* toxin-deficient strains," Infect Immun, Apr. 1995, 63(4):1369-72.

Price, B. M. et al., "Protection against anthrax lethal toxin challenge by genetic immunization with a plasmid encoding the lethal factor protein," Infect Immun, July 200169(7):4509-15.

Rudikoff et al., "Single amino acid substitution altering antigen-binding specificity," Proc Natl Acad Sci USA, 1982, vol. 79, pp. 1979-1983.

Rudinger et al., "Characteristics of the amino acids as components of a peptide hormone sequence," Jun. 1976, Peptide Hormones, Biological Council. Ed. By J.A. Parsons, University Park Press, pp. 5-7.

Sawada-Hirai, R. et al., "Human anti-anthrax protective antigen neutralizing monoclonal antibodies derived from donors vaccinated with anthrax vaccine adsorbed," J Immune Based Ther Vaccines, May 2004, 2(1):5.

Vajdos et al., "Comprehensive Functional Maps of the Antigen-binding Site of an Anti-ErbB2 Antibody Obtained with Shotgun Scanning Mutagenesis," J. of Molecular Biology, 2002, vol. 320, pp. 415-428.

Varughese, M. et al., "Internalization of a *Bacillus anthracis* protective antigen-c-Myc fusion protein mediated by cell surface anti-c-Myc antibodies," Mol Med, Feb. 1998, 4(2):87-95.

Vitale, L. et al., "Prophylaxis and therapy of inhalational anthrax by a novel monoclonal antibody to protective antigen that mimics vaccine-induced immunity," Infect Immun, Oct. 2006, 74(10):5840-7.

Wild, M. A. et al., "Human antibodies from immunized donors are protective against anthrax toxin in vivo," Nat Biotechnol, Nov. 2003, 21(11):1305-6; Epub Oct. 12, 2003.

Wu et al., "Humanization of a Murine Monoclonal Antibody by Simultaneous Optimization of Framework and CDR Residues," J. Mol. Biol., 1999, vol. 294, pp. 151-162.

Zhao, Ping et al., "Neutralizing monoclonal antibody against Anthrax lethal factor inhibits intoxication in a mouse model," Human Antibodies, vol. 12, No. 4, Jan. 1, 2003, pp. 129-135.

International Search Report and Written Opinion, dated Nov. 26, 2008, from PCT/US08/54609, filed Feb. 21, 2008.

|  |  | Framework 1 | CDR1 | Framework 2 | CDR2 |
|---|---|---|---|---|---|
| SEQ ID NO:49 | LF9D  | AEVQLLESGGGLVKPGGSLRLSCAASGFTFS | SYAMH | WVRQTPEKGLEWVS | TISSIGGSTW |
| SEQ ID NO:1  | LF10E | -------T---------------------- | ----- | ------A------- | S--GS--G--- |
| SEQ ID NO:17 | LF11H | RVQL-EQ--AEVK-P-ESLKI--KG--YS-T | N-WIG | ----M-G-----MG | I-YPDDSD-R |

|  |  | Framework 3 | CDR3 | Framework 4 |
|---|---|---|---|---|
|              | LF9D  | YSDSVKGRFTISRDNSKNTLFLHMKSLRAEDTAVYYCAR | DFFSQVGWSTPNNWFDP | WGQGTLVTVS |
|              | LF10E | -A-----------R--Y-QLN----------------- | PKYT**-YEN-***-Y | ---------- |
|              | LF11H | ---P-FQ-QV---F-K-I--AY-QWS--K-S----I-- | ALWFR*D-GKM****-V | --K-T----- |

*FIG. 1A*

|  |  | Framework 1 | CDR1 | Framework 2 | CDR2 |
|---|---|---|---|---|---|
| SEQ ID NO:50 | LF9D  | QAAELTQSPSTLSASVGDRVTITC | RASQGIATYLN | WYQQIPGKAPKLLIY | AASTLES |
| SEQ ID NO:9  | LF10E | AELQM-----S------------- | -D-RN--A--- | ----E-----R---- | Y--K-Q- |
| SEQ ID NO:25 | LF11H | AELQM-----S------------- | ----RND-G-- | --------K------ | ---S-Q- |

|  |  | Framework 3 | CDR3 | Framework 4 |
|---|---|---|---|---|
|              | LF9D  | GVPSRFSGSGSGAEFTLTISSLQPGDFATYYC | QQFYSMPLT | FGGGTKVEIKRT |
|              | LF10E | -----------R----TDYS-------E--- | --YD-V--- | -------M---- |
|              | LF11H | ----------------TD---------E--- | L-D-TY-W- | ---Q---L---- |

*FIG. 1B*

|  |  | Framework 1 | CDR1 | Framework 2 | CDR2 |
|---|---|---|---|---|---|
| SEQ ID NO:51 | EF12A | EGAAARVWGRLGKAWGFPETIVCSIWIHLSA | DYAMH | WVRQAPEKGLEWVS | SIID**GGAGTW |
| SEQ ID NO:33 | EF13D | -VQLL*ES-AEV-KP-SSVKVS-KVSGGTFS | SFGIS | ------GQ-----MG | L--P**ILGTAN |
| SEQ ID NO:52 | EF14H | -VQLLEES-GGLVKP-GSLR-S-AASGFTFS | N-S-N | ---------G----- | F-RTKAK-GTTE |
| SEQ ID NO:53 | EF15A | -VQLLEES-GGVQP-RSLR-S-TASGFTFS  | N-G-Q | ------G-R----A | F-S**YS-SNKQ |

|  |  | Framework 3 | CDR3 | Framework 4 |
|---|---|---|---|---|
|  | EF12A | SPDSVKGRFTISRDNAKNTLYLQMNSLRAEDTAVYYCVR | GVSGSYYVDHEY*** | WGQGTLVTVS |
|  | EF13D | YAQKFQ--L--TA-ESTS-V-MELS---S-------AT | D*PYHNWGEWDLD-**** | -------- |
|  | EF14H | YAA------------DSKSIA------KT-------TP | AGIIIRLVTPIYY-YMDV | --K--T--- |
|  | EF15A | YA---R---------S---I-------S--------A- | DSHYLDYLPDAFD-**** | -----V--- |

FIG. 2A

|  |  | Framework 1 | CDR1 | Framework 2 | CDR2 |
|---|---|---|---|---|---|
| SEQ ID NO:54 | EF12A | AAELTQSPATLSLSPGERATLSC | RASQSVSTYLA | WYQQRPGQSPRLLIY | GASNRAT |
| SEQ ID NO:41 | EF13D | ------SS--A-V-D-VSIT--- | ----I-N--S  | ----K--KA-Q--- | D--TLQS |
| SEQ ID NO:55 | EF14H | ------SS--A-V-D-V-IT--- | ----GIRN--- | ----K--KV-K--- | A--TLQS |
| SEQ ID NO:56 | EF15A | ELVM----SL--A-V-D-V-IT- | ----GISN--- | -F--K--KA-KR--F | T-YRLES |

|  |  | Framework 3 | CDR3 | Framework 4 |
|---|---|---|---|---|
|  | EF12A | GIPARFSGSGSGTDFTLTINSVEPEDFAVYYC | HQ*YDAQP*T | FGHGTRVDFKRT |
|  | EF13D | -V-S---------------S-LQ------T-- | QCG-GTY-*  | --G--Q-EI--- |
|  | EF14H | -V-S---------------S-LQ---V-T--- | QK*-SSA-F- | --P-K-GI--- |
|  | EF15A | -V-S-----M--E-----S-L-----T---  | L-*HSAY-P- | --Q--KLEI--- |

FIG. 2B

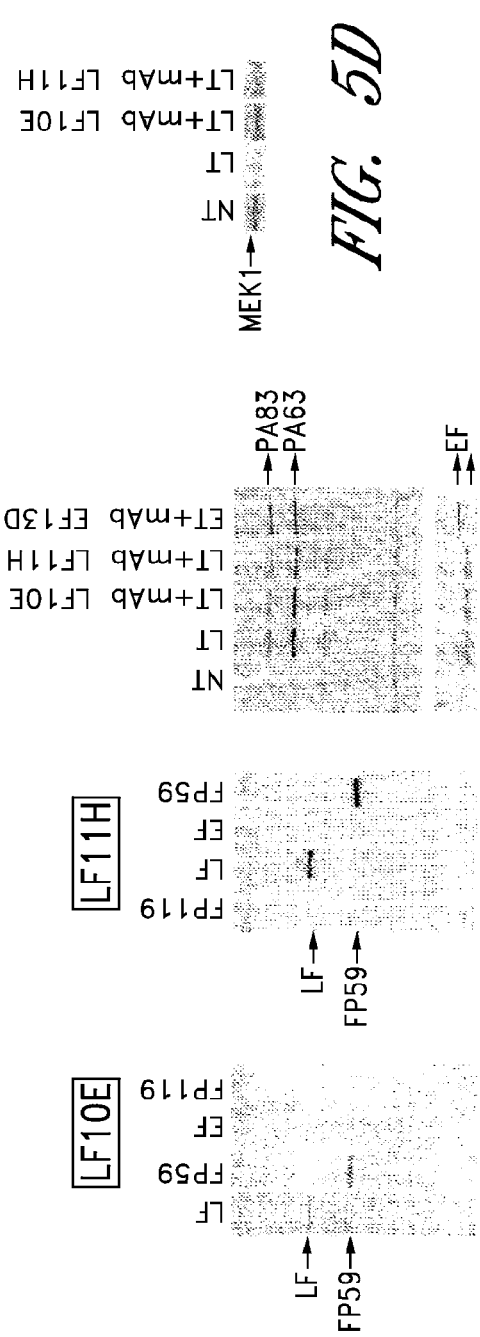

SEQUENCE LISTING

```
<160> NUMBER OF SEQ ID NOS: 66

<210> SEQ ID NO 1
<211> LENGTH: 121
<212> TYPE: PRT
<213> ORGANISM: Artificial Sequence
<220> FEATURE:
<223> OTHER INFORMATION: Monoclonal antibody
```

-continued

<400> SEQUENCE: 1

Ala Glu Val Gln Leu Leu Glu Ser Gly Gly Gly Leu Val Lys Pro Gly
1               5                   10                  15

Gly Ser Leu Arg Leu Thr Cys Ala Ala Ser Gly Phe Thr Phe Ser Ser
            20                  25                  30

Tyr Ala Met His Trp Val Arg Gln Ala Pro Glu Lys Gly Leu Glu Trp
        35                  40                  45

Val Ser Ser Ile Ser Gly Ser Gly Gly Thr Trp Tyr Ala Asp Ser
    50                  55                  60

Val Lys Gly Arg Phe Thr Ile Ser Arg Asp Asn Ser Arg Asn Thr Leu
65                  70                  75                  80

Tyr Leu Gln Leu Asn Ser Leu Arg Ala Glu Asp Thr Ala Val Tyr Tyr
                85                  90                  95

Cys Ala Arg Pro Lys Tyr Thr Gly Tyr Glu Asn Pro Phe Asp Tyr Trp
            100                 105                 110

Gly Gln Gly Thr Leu Val Thr Val Ser
        115                 120

<210> SEQ ID NO 2
<211> LENGTH: 31
<212> TYPE: PRT
<213> ORGANISM: Artificial Sequence
<220> FEATURE:
<223> OTHER INFORMATION: Monoclonal antibody

<400> SEQUENCE: 2

Ala Glu Val Gln Leu Leu Glu Ser Gly Gly Gly Leu Val Lys Pro Gly
1               5                   10                  15

Gly Ser Leu Arg Leu Thr Cys Ala Ala Ser Gly Phe Thr Phe Ser
            20                  25                  30

<210> SEQ ID NO 3
<211> LENGTH: 5
<212> TYPE: PRT
<213> ORGANISM: Artificial Sequence
<220> FEATURE:
<223> OTHER INFORMATION: Monoclonal antibody

<400> SEQUENCE: 3

Ser Tyr Ala Met His
1               5

<210> SEQ ID NO 4
<211> LENGTH: 14
<212> TYPE: PRT
<213> ORGANISM: Artificial Sequence
<220> FEATURE:
<223> OTHER INFORMATION: Monoclonal antibody

<400> SEQUENCE: 4

Trp Val Arg Gln Ala Pro Glu Lys Gly Leu Glu Trp Val Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Monoclonal antibody

```
<400> SEQUENCE: 5

Ser Ile Ser Gly Ser Gly Gly Thr Trp
1               5                   10

<210> SEQ ID NO 6
<211> LENGTH: 39
<212> TYPE: PRT
<213> ORGANISM: Artificial Sequence
<220> FEATURE:
<223> OTHER INFORMATION: Monoclonal antibody

<400> SEQUENCE: 6

Tyr Ala Asp Ser Val Lys Gly Arg Phe Thr Ile Ser Arg Asp Asn Ser
1               5                   10                  15

Arg Asn Thr Leu Tyr Leu Gln Leu Asn Ser Leu Arg Ala Glu Asp Thr
            20                  25                  30

Ala Val Tyr Tyr Cys Ala Arg
        35

<210> SEQ ID NO 7
<211> LENGTH: 12
<212> TYPE: PRT
<213> ORGANISM: Artificial Sequence
<220> FEATURE:
<223> OTHER INFORMATION: Monoclonal antibody

<400> SEQUENCE: 7

Pro Lys Tyr Thr Gly Tyr Glu Asn Pro Phe Asp Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Monoclonal antibody

<400> SEQUENCE: 8

Trp Gly Gln Gly Thr Leu Val Thr Val Ser
1               5                   10

<210> SEQ ID NO 9
<211> LENGTH: 110
<212> TYPE: PRT
<213> ORGANISM: Artificial Sequence
<220> FEATURE:
<223> OTHER INFORMATION: Monoclonal antibody

<400> SEQUENCE: 9

Ala Glu Leu Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Arg Asn
            20                  25                  30

Tyr Leu Ala Trp Tyr Gln Gln Glu Pro Gly Lys Ala Pro Arg Leu Leu
        35                  40                  45

Ile Tyr Tyr Ala Ser Lys Leu Gln Ser Gly Val Pro Ser Arg Phe Ser
    50                  55                  60

Gly Arg Gly Ser Gly Thr Asp Tyr Ser Leu Thr Ile Ser Ser Leu Gln
65                  70                  75                  80
```

```
Pro Glu Asp Phe Ala Thr Tyr Tyr Cys Gln Gln Tyr Asp Ser Val Pro
            85                  90                  95

Leu Thr Phe Gly Gly Gly Thr Lys Met Glu Ile Lys Arg Thr
            100                 105                 110

<210> SEQ ID NO 10
<211> LENGTH: 24
<212> TYPE: PRT
<213> ORGANISM: Artificial Sequence
<220> FEATURE:
<223> OTHER INFORMATION: Monoclonal antibody

<400> SEQUENCE: 10

Ala Glu Leu Gln Met Thr Gln Ser Pro Ser Ser Leu Ser Ala Ser Val
1               5                   10                  15

Gly Asp Arg Val Thr Ile Thr Cys
            20

<210> SEQ ID NO 11
<211> LENGTH: 11
<212> TYPE: PRT
<213> ORGANISM: Artificial Sequence
<220> FEATURE:
<223> OTHER INFORMATION: Monoclonal antibody

<400> SEQUENCE: 11

Arg Ala Ser Gln Asp Ile Arg Asn Tyr Leu Ala
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Monoclonal antibody

<400> SEQUENCE: 12

Trp Tyr Gln Gln Glu Pro Gly Lys Ala Pro Arg Leu Leu Ile Tyr
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Monoclonal antibody

<400> SEQUENCE: 13

Tyr Ala Ser Lys Leu Gln Ser
1               5

<210> SEQ ID NO 14
<211> LENGTH: 32
<212> TYPE: PRT
<213> ORGANISM: Artificial Sequence
<220> FEATURE:
<223> OTHER INFORMATION: Monoclonal antibody

<400> SEQUENCE: 14

Gly Val Pro Ser Arg Phe Ser Gly Arg Gly Ser Gly Thr Asp Tyr Ser
1               5                   10                  15

Leu Thr Ile Ser Ser Leu Gln Pro Glu Asp Phe Ala Thr Tyr Tyr Cys
            20                  25                  30
```

```
<210> SEQ ID NO 15
<211> LENGTH: 9
<212> TYPE: PRT
<213> ORGANISM: Artificial Sequence
<220> FEATURE:
<223> OTHER INFORMATION: Monoclonal antibody

<400> SEQUENCE: 15

Gln Gln Tyr Asp Ser Val Pro Leu Thr
 1               5

<210> SEQ ID NO 16
<211> LENGTH: 12
<212> TYPE: PRT
<213> ORGANISM: Artificial Sequence
<220> FEATURE:
<223> OTHER INFORMATION: Monoclonal antibody

<400> SEQUENCE: 16

Phe Gly Gly Gly Thr Lys Met Glu Ile Lys Arg Thr
 1               5                  10

<210> SEQ ID NO 17
<211> LENGTH: 121
<212> TYPE: PRT
<213> ORGANISM: Artificial Sequence
<220> FEATURE:
<223> OTHER INFORMATION: Monoclonal antibody

<400> SEQUENCE: 17

Arg Val Gln Leu Leu Glu Gln Ser Gly Ala Glu Val Lys Lys Pro Gly
 1               5                  10                  15

Glu Ser Leu Lys Ile Ser Cys Lys Gly Ser Gly Tyr Ser Phe Thr Asn
             20                  25                  30

Tyr Trp Ile Gly Trp Val Arg Gln Met Pro Gly Lys Gly Leu Glu Trp
         35                  40                  45

Met Gly Ile Ile Tyr Pro Asp Asp Ser Asp Thr Arg Tyr Ser Pro Ser
     50                  55                  60

Phe Gln Gly Gln Val Thr Ile Ser Phe Asp Lys Ser Ile Asn Thr Ala
 65                  70                  75                  80

Tyr Leu Gln Trp Ser Ser Leu Lys Ala Ser Asp Thr Ala Ile Tyr Tyr
                 85                  90                  95

Cys Ala Arg Ala Leu Trp Phe Arg Asp Trp Gly Lys Met Asp Val Trp
            100                 105                 110

Gly Lys Gly Thr Thr Val Thr Val Ser
        115                 120

<210> SEQ ID NO 18
<211> LENGTH: 31
<212> TYPE: PRT
<213> ORGANISM: Artificial Sequence
<220> FEATURE:
<223> OTHER INFORMATION: Monoclonal antibody

<400> SEQUENCE: 18

Arg Val Gln Leu Leu Glu Gln Ser Gly Ala Glu Val Lys Lys Pro Gly
 1               5                  10                  15

Glu Ser Leu Lys Ile Ser Cys Lys Gly Ser Gly Tyr Ser Phe Thr
             20                  25                  30
```

```
<210> SEQ ID NO 19
<211> LENGTH: 5
<212> TYPE: PRT
<213> ORGANISM: Artificial Sequence
<220> FEATURE:
<223> OTHER INFORMATION: Monoclonal antibody

<400> SEQUENCE: 19

Asn Tyr Trp Ile Gly
 1               5

<210> SEQ ID NO 20
<211> LENGTH: 14
<212> TYPE: PRT
<213> ORGANISM: Artificial Sequence
<220> FEATURE:
<223> OTHER INFORMATION: Monoclonal antibody

<400> SEQUENCE: 20

Trp Val Arg Gln Met Pro Gly Lys Gly Leu Glu Trp Met Gly
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: Monoclonal antibody

<400> SEQUENCE: 21

Ile Ile Tyr Pro Asp Asp Ser Asp Thr Arg
 1               5                  10

<210> SEQ ID NO 22
<211> LENGTH: 39
<212> TYPE: PRT
<213> ORGANISM: Artificial Sequence
<220> FEATURE:
<223> OTHER INFORMATION: Monoclonal antibody

<400> SEQUENCE: 22

Tyr Ser Pro Ser Phe Gln Gly Gln Val Thr Ile Ser Phe Asp Lys Ser
 1               5                  10                  15

Ile Asn Thr Ala Tyr Leu Gln Trp Ser Ser Leu Lys Ala Ser Asp Thr
            20                  25                  30

Ala Ile Tyr Tyr Cys Ala Arg
        35

<210> SEQ ID NO 23
<211> LENGTH: 12
<212> TYPE: PRT
<213> ORGANISM: Artificial Sequence
<220> FEATURE:
<223> OTHER INFORMATION: Monoclonal antibody

<400> SEQUENCE: 23

Ala Leu Trp Phe Arg Asp Trp Gly Lys Met Asp Val
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: Monoclonal antibody
```

```
<400> SEQUENCE: 24

Trp Gly Lys Gly Thr Thr Val Thr Val Ser
1               5                  10

<210> SEQ ID NO 25
<211> LENGTH: 110
<212> TYPE: PRT
<213> ORGANISM: Artificial Sequence
<220> FEATURE:
<223> OTHER INFORMATION: Monoclonal antibody

<400> SEQUENCE: 25

Ala Glu Leu Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Asp Leu Gly Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gln Asp Tyr Thr Tyr Pro
                85                  90                  95

Trp Thr Phe Gly Gln Gly Thr Lys Leu Glu Ile Lys Arg Thr
            100                 105                 110

<210> SEQ ID NO 26
<211> LENGTH: 24
<212> TYPE: PRT
<213> ORGANISM: Artificial Sequence
<220> FEATURE:
<223> OTHER INFORMATION: Monoclonal antibody

<400> SEQUENCE: 26

Ala Glu Leu Gln Met Thr Gln Ser Pro Ser Ser Leu Ser Ala Ser Val
1               5                   10                  15

Gly Asp Arg Val Thr Ile Thr Cys
            20

<210> SEQ ID NO 27
<211> LENGTH: 11
<212> TYPE: PRT
<213> ORGANISM: Artificial Sequence
<220> FEATURE:
<223> OTHER INFORMATION: Monoclonal antibody

<400> SEQUENCE: 27

Arg Ala Ser Gln Gly Ile Arg Asn Asp Leu Gly
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Monoclonal antibody

<400> SEQUENCE: 28

Trp Tyr Gln Gln Lys Pro Gly Lys Ala Pro Lys Leu Leu Ile Tyr
1               5                   10                  15
```

-continued

```
<210> SEQ ID NO 29
<211> LENGTH: 7
<212> TYPE: PRT
<213> ORGANISM: Artificial Sequence
<220> FEATURE:
<223> OTHER INFORMATION: Monoclonal antibody

<400> SEQUENCE: 29

Ala Ala Ser Ser Leu Gln Ser
1               5

<210> SEQ ID NO 30
<211> LENGTH: 32
<212> TYPE: PRT
<213> ORGANISM: Artificial Sequence
<220> FEATURE:
<223> OTHER INFORMATION: Monoclonal antibody

<400> SEQUENCE: 30

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 31
<211> LENGTH: 9
<212> TYPE: PRT
<213> ORGANISM: Artificial Sequence
<220> FEATURE:
<223> OTHER INFORMATION: Monoclonal antibody

<400> SEQUENCE: 31

Leu Gln Asp Tyr Thr Tyr Pro Trp Thr
1               5

<210> SEQ ID NO 32
<211> LENGTH: 12
<212> TYPE: PRT
<213> ORGANISM: Artificial Sequence
<220> FEATURE:
<223> OTHER INFORMATION: Monoclonal antibody

<400> SEQUENCE: 32

Phe Gly Gln Gly Thr Lys Leu Glu Ile Lys Arg Thr
1               5                   10

<210> SEQ ID NO 33
<211> LENGTH: 121
<212> TYPE: PRT
<213> ORGANISM: Artificial Sequence
<220> FEATURE:
<223> OTHER INFORMATION: Monoclonal antibody

<400> SEQUENCE: 33

Glu Val Gln Leu Leu Glu Ser Gly Ala Glu Val Lys Lys Pro Gly Ser
1               5                   10                  15

Ser Val Lys Val Ser Cys Lys Val Ser Gly Gly Thr Phe Ser Ser Phe
            20                  25                  30

Gly Ile Ser Trp Val Arg Gln Ala Pro Gly Gln Gly Leu Glu Trp Met
        35                  40                  45

Gly Leu Ile Ile Pro Ile Leu Gly Thr Ala Asn Tyr Ala Gln Lys Phe
    50                  55                  60

Gln Gly Arg Leu Thr Ile Thr Ala Asp Glu Ser Thr Ser Thr Val Tyr
65                  70                  75                  80
```

Met Glu Leu Ser Ser Leu Arg Ser Glu Asp Thr Ala Val Tyr Tyr Cys
                85                  90                  95

Ala Thr Asp Pro Tyr His Asn Trp Gly Glu Trp Asp Leu Asp Tyr Trp
            100                 105                 110

Gly Gln Gly Thr Leu Val Thr Val Ser
        115                 120

<210> SEQ ID NO 34
<211> LENGTH: 30
<212> TYPE: PRT
<213> ORGANISM: Artificial Sequence
<220> FEATURE:
<223> OTHER INFORMATION: Monoclonal antibody

<400> SEQUENCE: 34

Glu Val Gln Leu Leu Glu Ser Gly Ala Glu Val Lys Lys Pro Gly Ser
1               5                   10                  15

Ser Val Lys Val Ser Cys Lys Val Ser Gly Gly Thr Phe Ser
            20                  25                  30

<210> SEQ ID NO 35
<211> LENGTH: 5
<212> TYPE: PRT
<213> ORGANISM: Artificial Sequence
<220> FEATURE:
<223> OTHER INFORMATION: Monoclonal antibody

<400> SEQUENCE: 35

Ser Phe Gly Ile Ser
1               5

<210> SEQ ID NO 36
<211> LENGTH: 14
<212> TYPE: PRT
<213> ORGANISM: Artificial Sequence
<220> FEATURE:
<223> OTHER INFORMATION: Monoclonal antibody

<400> SEQUENCE: 36

Trp Val Arg Gln Ala Pro Gly Gln Gly Leu Glu Trp Met Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Monoclonal antibody

<400> SEQUENCE: 37

Leu Ile Ile Pro Ile Leu Gly Thr Ala Asn
1               5                   10

<210> SEQ ID NO 38
<211> LENGTH: 39
<212> TYPE: PRT
<213> ORGANISM: Artificial Sequence
<220> FEATURE:
<223> OTHER INFORMATION: Monoclonal antibody

```
<400> SEQUENCE: 38

Tyr Ala Gln Lys Phe Gln Gly Arg Leu Thr Ile Thr Ala Asp Glu Ser
1               5                   10                  15

Thr Ser Thr Val Tyr Met Glu Leu Ser Ser Leu Arg Ser Glu Asp Thr
            20                  25                  30

Ala Val Tyr Tyr Cys Ala Thr
            35

<210> SEQ ID NO 39
<211> LENGTH: 13
<212> TYPE: PRT
<213> ORGANISM: Artificial Sequence
<220> FEATURE:
<223> OTHER INFORMATION: Monoclonal antibody

<400> SEQUENCE: 39

Asp Pro Tyr His Asn Trp Gly Glu Trp Asp Leu Asp Tyr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Monoclonal antibody

<400> SEQUENCE: 40

Trp Gly Gln Gly Thr Leu Val Thr Val Ser
1               5                   10

<210> SEQ ID NO 41
<211> LENGTH: 109
<212> TYPE: PRT
<213> ORGANISM: Artificial Sequence
<220> FEATURE:
<223> OTHER INFORMATION: Monoclonal antibody

<400> SEQUENCE: 41

Ala Ala Glu Leu Thr Gln Ser Pro Ser Ser Leu Ser Ala Ser Val Gly
1               5                   10                  15

Asp Arg Val Ser Ile Thr Cys Arg Ala Ser Gln Ser Ile Ser Asn Tyr
            20                  25                  30

Leu Ser Trp Tyr Gln Gln Lys Pro Gly Lys Ala Pro Gln Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Gly Tyr Gly Thr Tyr Pro
                85                  90                  95

Thr Phe Gly Gly Gly Thr Gln Val Glu Ile Lys Arg Thr
            100                 105

<210> SEQ ID NO 42
<211> LENGTH: 23
<212> TYPE: PRT
<213> ORGANISM: Artificial Sequence
<220> FEATURE:
<223> OTHER INFORMATION: Monoclonal antibody
```

```
<400> SEQUENCE: 42

Ala Ala Glu Leu Thr Gln Ser Pro Ser Ser Leu Ser Ala Ser Val Gly
1               5                   10                  15

Asp Arg Val Ser Ile Thr Cys
            20

<210> SEQ ID NO 43
<211> LENGTH: 11
<212> TYPE: PRT
<213> ORGANISM: Artificial Sequence
<220> FEATURE:
<223> OTHER INFORMATION: Monoclonal antibody

<400> SEQUENCE: 43

Arg Ala Ser Gln Ser Ile Ser Asn Tyr Leu Ser
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Monoclonal antibody

<400> SEQUENCE: 44

Trp Tyr Gln Gln Lys Pro Gly Lys Ala Pro Gln Leu Leu Ile Tyr
1               5                   10                  15

<210> SEQ ID NO 45
<211> LENGTH: 7
<212> TYPE: PRT
<213> ORGANISM: Artificial Sequence
<220> FEATURE:
<223> OTHER INFORMATION: Monoclonal antibody

<400> SEQUENCE: 45

Asp Ala Ser Thr Leu Gln Ser
1               5

<210> SEQ ID NO 46
<211> LENGTH: 32
<212> TYPE: PRT
<213> ORGANISM: Artificial Sequence
<220> FEATURE:
<223> OTHER INFORMATION: Monoclonal antibody

<400> SEQUENCE: 46

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 47
<211> LENGTH: 9
<212> TYPE: PRT
<213> ORGANISM: Artificial Sequence
<220> FEATURE:
<223> OTHER INFORMATION: Monoclonal antibody

<400> SEQUENCE: 47

Gln Cys Gly Tyr Gly Thr Tyr Pro Thr
1               5
```

```
<210> SEQ ID NO 48
<211> LENGTH: 12
<212> TYPE: PRT
<213> ORGANISM: Artificial Sequence
<220> FEATURE:
<223> OTHER INFORMATION: Monoclonal antibody

<400> SEQUENCE: 48

Phe Gly Gly Gly Thr Gln Val Glu Ile Lys Arg Thr
 1               5                  10

<210> SEQ ID NO 49
<211> LENGTH: 126
<212> TYPE: PRT
<213> ORGANISM: Artificial Sequence
<220> FEATURE:
<223> OTHER INFORMATION: Monoclonal antibody

<400> SEQUENCE: 49

Ala Glu Val Gln Leu Leu Glu Ser Gly Gly Leu Val Lys Pro Gly
 1               5                  10                  15

Gly Ser Leu Arg Leu Ser Cys Ala Ala Ser Gly Phe Thr Phe Ser Ser
                20                  25                  30

Tyr Ala Met His Trp Val Arg Gln Thr Pro Glu Lys Gly Leu Glu Trp
            35                  40                  45

Val Ser Thr Ile Ser Ser Ile Gly Gly Ser Thr Trp Tyr Ser Asp Ser
50                  55                  60

Val Lys Gly Arg Phe Thr Ile Ser Arg Asp Asn Ser Lys Asn Thr Leu
65                  70                  75                  80

Phe Leu His Met Lys Ser Leu Arg Ala Glu Asp Thr Ala Val Tyr Tyr
                85                  90                  95

Cys Ala Arg Asp Phe Phe Ser Gln Val Gly Trp Ser Thr Pro Asn Asn
            100                 105                 110

Trp Phe Asp Pro Trp Gly Gln Gly Thr Leu Val Thr Val Ser
            115                 120                 125

<210> SEQ ID NO 50
<211> LENGTH: 110
<212> TYPE: PRT
<213> ORGANISM: Artificial Sequence
<220> FEATURE:
<223> OTHER INFORMATION: Monoclonal antibody

<400> SEQUENCE: 50

Gln Ala Ala Glu Leu Thr Gln Ser Pro Ser Thr Leu Ser Ala Ser Val
 1               5                  10                  15

Gly Asp Arg Val Thr Ile Thr Cys Arg Ala Ser Gln Gly Ile Ala Thr
                20                  25                  30

Tyr Leu Asn Trp Tyr Gln Gln Ile Pro Gly Lys Ala Pro Lys Leu Leu
            35                  40                  45

Ile Tyr Ala Ala Ser Thr Leu Glu Ser Gly Val Pro Ser Arg Phe Ser
50                  55                  60

Gly Ser Gly Ser Gly Ala Glu Phe Thr Leu Thr Ile Ser Ser Leu Gln
65                  70                  75                  80

Pro Gly Asp Phe Ala Thr Tyr Tyr Cys Gln Gln Phe Tyr Ser Met Pro
                85                  90                  95

Leu Thr Phe Gly Gly Gly Thr Lys Val Glu Ile Lys Arg Thr
            100                 105                 110
```

```
<210> SEQ ID NO 51
<211> LENGTH: 121
<212> TYPE: PRT
<213> ORGANISM: Artificial Sequence
<220> FEATURE:
<223> OTHER INFORMATION: Monoclonal antibody

<400> SEQUENCE: 51

Glu Gly Ala Ala Ala Arg Val Trp Gly Arg Leu Gly Lys Ala Trp Gly
 1               5                  10                  15

Phe Pro Glu Thr Leu Val Cys Ser Leu Trp Ile His Leu Ser Ala Asp
            20                  25                  30

Tyr Ala Met His Trp Val Arg Gln Ala Pro Glu Lys Gly Leu Glu Trp
        35                  40                  45

Val Ser Ser Ile Ile Asp Gly Ala Gly Thr Trp Ser Pro Asp Ser
    50                  55                  60

Val Lys Gly Arg Phe Thr Ile Ser Arg Asp Asn Ala Lys Asn Thr Leu
 65                  70                  75                  80

Tyr Leu Gln Met Asn Ser Leu Arg Ala Glu Asp Thr Ala Val Tyr Tyr
                85                  90                  95

Cys Val Arg Gly Val Ser Gly Ser Tyr Tyr Val Asp His Glu Tyr Trp
            100                 105                 110

Gly Gln Gly Thr Leu Val Thr Val Ser
        115                 120

<210> SEQ ID NO 52
<211> LENGTH: 129
<212> TYPE: PRT
<213> ORGANISM: Artificial Sequence
<220> FEATURE:
<223> OTHER INFORMATION: Monoclonal antibody

<400> SEQUENCE: 52

Glu Val Gln Leu Leu Glu Ser Gly Gly Leu Val Lys Pro Gly
 1               5                  10                  15

Gly Ser Leu Arg Leu Ser Cys Ala Ala Ser Gly Phe Thr Phe Ser Asn
            20                  25                  30

Tyr Ser Met Asn Trp Val Arg Gln Ala Pro Gly Lys Gly Leu Glu Trp
        35                  40                  45

Val Gly Phe Ile Arg Thr Lys Ala Lys Gly Gly Thr Thr Glu Tyr Ala
    50                  55                  60

Ala Ser Val Lys Gly Arg Phe Thr Ile Ser Arg Asp Asp Ser Lys Ser
 65                  70                  75                  80

Ile Ala Tyr Leu Gln Met Asn Ser Leu Lys Thr Glu Asp Thr Ala Val
                85                  90                  95

Tyr Tyr Cys Thr Pro Ala Gly Ile Ile Ile Arg Leu Val Thr Pro Ile
            100                 105                 110

Tyr Tyr Tyr Tyr Met Asp Val Trp Gly Lys Gly Thr Thr Val Thr Val
        115                 120                 125

Ser

<210> SEQ ID NO 53
<211> LENGTH: 123
<212> TYPE: PRT
<213> ORGANISM: Artificial Sequence
<220> FEATURE:
<223> OTHER INFORMATION: Monoclonal antibody
```

```
<400> SEQUENCE: 53

Glu Val Gln Leu Leu Glu Glu Ser Gly Gly Val Val Gln Pro Gly
1               5                   10                  15

Arg Ser Leu Arg Leu Ser Cys Thr Ala Ser Gly Phe Thr Phe Ser Asn
            20                  25                  30

Tyr Gly Met Gln Trp Val Arg Gln Ala Pro Gly Lys Arg Leu Glu Trp
                35                  40                  45

Val Ala Phe Ile Ser Tyr Ser Gly Ser Asn Lys Gln Tyr Ala Asp Ser
    50                  55                  60

Val Arg Gly Arg Phe Thr Ile Ser Arg Asp Asn Ser Lys Asn Ile Leu
65                  70                  75                  80

Tyr Leu Gln Met Asn Ser Leu Arg Ser Glu Asp Thr Ala Val Tyr Tyr
                85                  90                  95

Cys Ala Arg Asp Ser His Tyr Leu Asp Tyr Leu Pro Asp Ala Phe Asp
                100                 105                 110

Tyr Trp Gly Gln Gly Thr Val Val Thr Val Ser
            115                 120
```

```
<210> SEQ ID NO 54
<211> LENGTH: 108
<212> TYPE: PRT
<213> ORGANISM: Artificial Sequence
<220> FEATURE:
<223> OTHER INFORMATION: Monoclonal antibody

<400> SEQUENCE: 54

Ala Ala Glu Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Tyr
            20                  25                  30

Leu Ala Trp Tyr Gln Gln Arg Pro Gly Gln Ser Pro Arg Leu Leu Ile
                35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Asn Ser Val Glu Pro
65                  70                  75                  80

Glu Asp Phe Ala Val Tyr Tyr Cys His Gln Tyr Asp Ala Gln Pro Thr
                85                  90                  95

Phe Gly His Gly Thr Arg Val Asp Phe Lys Arg Thr
                100                 105
```

```
<210> SEQ ID NO 55
<211> LENGTH: 109
<212> TYPE: PRT
<213> ORGANISM: Artificial Sequence
<220> FEATURE:
<223> OTHER INFORMATION: Monoclonal antibody

<400> SEQUENCE: 55

Ala Ala Glu Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Val Pro Lys Leu Leu Ile
                35                  40                  45

Tyr Ala Ala Ser Thr Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Ser Ser Ala Pro Phe
                 85                  90                  95

Thr Phe Gly Pro Gly Thr Lys Val Gly Ile Lys Arg Thr
            100                 105

<210> SEQ ID NO 56
<211> LENGTH: 109
<212> TYPE: PRT
<213> ORGANISM: Artificial Sequence
<220> FEATURE:
<223> OTHER INFORMATION: Monoclonal antibody

<400> SEQUENCE: 56

Glu Leu Val Met Thr Gln Ser Pro Ser Leu Leu Ser Ala Ser Val Gly
  1               5                  10                  15

Asp Arg Val Thr Ile Thr Cys Arg Ala Ser Gln Gly Ile Ser Asn Tyr
                 20                  25                  30

Leu Ala Trp Phe Gln Gln Lys Pro Gly Lys Ala Pro Lys Arg Leu Ile
             35                  40                  45

Phe Thr Ala Tyr Arg Leu Glu Ser Gly Val Pro Ser Arg Phe Ser Gly
 50                  55                  60

Ser Met Ser Gly Thr Glu Phe Thr Leu Thr Ile Ser Ser Leu Glu Pro
 65                  70                  75                  80

Glu Asp Phe Ala Thr Tyr Tyr Cys Leu Gln His Ser Ala Tyr Pro Pro
                 85                  90                  95

Thr Phe Gly Gln Gly Thr Lys Leu Glu Ile Lys Arg Thr
            100                 105

<210> SEQ ID NO 57
<211> LENGTH: 363
<212> TYPE: DNA
<213> ORGANISM: Artificial Sequence
<220> FEATURE:
<223> OTHER INFORMATION: Monoclonal antibody

<400> SEQUENCE: 57
gccgaggtgc agctgctcga gtctggggga ggcttggtga agcctggggg ttccctgaga    60
ctcacgtgtg cagcctctgg attcaccttc agtagctatg ctatgcactg ggtccgccag   120
gctccagaga agggactgga gtgggtctca agtattagtg gtagtggtgg tggcacgtgg   180
tacgcagact ctgtcaaggg ccgattcacc atctccagag acaattccag gaacacgctg   240
tatctgcagc tgaacagcct gagagccgag gacacggccg tgtattactg tgcgagacct   300
aaatacactg gctacgagaa tcctttttgac tactggggcc agggaacccct tgtcaccgtc   360 tcc                                                                 363

<210> SEQ ID NO 58
<211> LENGTH: 330
<212> TYPE: DNA
<213> ORGANISM: Artificial Sequence
<220> FEATURE:
<223> OTHER INFORMATION: Monoclonal antibody

<400> SEQUENCE: 58
gccgagctcc agatgaccca gtctccatcc tccctgtctg catctgtagg agacagagtc    60
accatcactt gccgggccag tcaggacatt agaaattatt tggcctggta tcagcaggaa   120
ccagggaaag cccctaggct cctcatctat tatgcatcca agttacaaag tggggttcca   180
```

```
tcaaggttca gcggcagagg gtctgggacg gattactctc tcaccatcag cagcctgcag    240
cctgaagatt ttgcaactta ttactgtcaa cagtatgaca gtgtcccgct cactttcggt    300
ggagggacca agatggagat caaacgaact                                     330
```

<210> SEQ ID NO 59
<211> LENGTH: 411
<212> TYPE: DNA
<213> ORGANISM: Artificial Sequence
<220> FEATURE:
<223> OTHER INFORMATION: Monoclonal antibody

<400> SEQUENCE: 59

```
agggtgcagc tgctcgagca gtctggggca gaggtgaaaa agcccgggga gtctctgaaa     60
atctcctgta agggctctgg atacagcttt accaactact ggatcggctg ggtgcgccag    120
atgcccggga aaggcctaga gtggatgggg atcatctatc ctgatgactc tgataccaga    180
tatagcccgt ccttccaagg ccaggtcacc atctcattcg acaagtccat caacaccgcc    240
tacctgcagt ggagcagcct gaaggcctcg gacaccgcca tatattactg tgcgagggcc    300
ttatggttca gggactgggg caagatggac gtctgggca aagggaccac ggtcaccgtc     360
tcctcagcct ccaccaaggg cccatcggtc ttcccctgg cgccctcctc c              411
```

<210> SEQ ID NO 60
<211> LENGTH: 330
<212> TYPE: DNA
<213> ORGANISM: Artificial Sequence
<220> FEATURE:
<223> OTHER INFORMATION: Monoclonal antibody

<400> SEQUENCE: 60

```
gccgagctcc agatgaccca gtctccatcc tccctgtctg catctgtggg agacagagtc     60
accatcactt gccgggcaag tcagggcatt agaaacgatt taggctggta tcagcagaag    120
ccagggaaag cccctaagct cctgatctat gctgcttcca gtttacaaag tggagtccca    180
tcaaggttca gtggcagtgg atctggcaca gatttcactc tcaccatcag cagcctgcag    240
cctgaagatt ttgcaactta ttactgtcta caggattaca cttacccgtg gacgttcggc    300
caagggacca gctggaaat caaacgaact                                      330
```

<210> SEQ ID NO 61
<211> LENGTH: 363
<212> TYPE: DNA
<213> ORGANISM: Artificial Sequence
<220> FEATURE:
<223> OTHER INFORMATION: Monoclonal antibody

<400> SEQUENCE: 61

```
gaggtgcagc tgctcgagtc tggggctgag gtgaagaagc ctgggtcttc agtgaaggtc     60
tcctgcaagg tttctggagg caccttcagc agctttggta tcagctgggt gcgacaggcc    120
cctggacaag gcttgagtg gatgggattg atcatcccta tccttggtac agcaaactac    180
gcacagaagt tccagggcag actcacgatt accgcggacg aatccacgag cacagtctac    240
atggagctga gcagcctgag atctgaggac acggccgtgt attactgtgc gacagacccc    300
taccataatt ggggggagtg ggaccttgac tactggggcc agggaaccct ggtcaccgtc    360
tcc                                                                  363
```

<210> SEQ ID NO 62
<211> LENGTH: 327
<212> TYPE: DNA
<213> ORGANISM: Artificial Sequence
<220> FEATURE:
<223> OTHER INFORMATION: Monoclonal antibody

<400> SEQUENCE: 62

```
gcggccgagc tcacccagtc tccatcctcc ctgtctgcat ctgtaggaga cagagtcagt    60
atcacttgcc gggcaagtca gagcattagc aactatttga gttggtatca gcagaaacca   120
gggaaagccc ctcagctcct gatctatgat gcatccactt tacaaagtgg ggtcccatca   180
aggttcagtg gcagtggatc tgggacagat ttcactctca ccatcagcag tctgcagcct   240
gaagattttg caacatatta ctgtcagtgt ggttacggta catatcccac tttcggtgga   300
gggacccagg tggagatcaa acgaact                                       327
```

<210> SEQ ID NO 63
<211> LENGTH: 121
<212> TYPE: PRT
<213> ORGANISM: Artificial Sequence
<220> FEATURE:
<223> OTHER INFORMATION: Monoclonal antibody

<400> SEQUENCE: 63

Glu Val Gln Leu Leu Glu Thr Gly Gly Gly Leu Val Gln Pro Gly Gly
 1               5                  10                  15

Ser Leu Arg Leu Ser Cys Ala Ala Ser Gly Phe Thr Leu Arg Ser Tyr
            20                  25                  30

His Met Ser Trp Val Arg Arg Ala Pro Gly Lys Gly Leu Glu Trp Val
        35                  40                  45

Ser Val Ile Tyr Asp Gly Gly Ser Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Thr Ser Leu Arg Ala Glu Asp Thr Ala Val Tyr Tyr Cys Ala
                85                  90                  95

Arg Ser Gly Arg Pro Leu Gln Asn Tyr Tyr Tyr Met Asp Val Trp Gly
            100                 105                 110

Lys Gly Thr Thr Val Thr Val Ser Ser
        115                 120

<210> SEQ ID NO 64
<211> LENGTH: 113
<212> TYPE: PRT
<213> ORGANISM: Artificial Sequence
<220> FEATURE:
<223> OTHER INFORMATION: Monoclonal antibody

<400> SEQUENCE: 64

Glu Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Arg Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Glu Ile Lys
            100                 105                 110

Arg

<210> SEQ ID NO 65
<211> LENGTH: 121
<212> TYPE: PRT
<213> ORGANISM: Artificial Sequence
<220> FEATURE:
<223> OTHER INFORMATION: Monoclonal antibody

<400> SEQUENCE: 65

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

His Met Ser Trp Val Arg Lys Ala Pro Gly Lys Gly Leu Glu Trp Val
        35                  40                  45

Ser Val Ile Tyr Asp Gly Gly Ser Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Thr Ser Leu Arg Ala Glu Asp Thr Ala Val Tyr Tyr Cys Ala
                85                  90                  95

Arg Ser Gly Arg Pro Leu Gln Asn Tyr Tyr Tyr Met Asp Val Trp Gly
            100                 105                 110

Lys Gly Thr Thr Val Thr Val Ser Ser
        115                 120

<210> SEQ ID NO 66
<211> LENGTH: 113
<212> TYPE: PRT
<213> ORGANISM: Artificial Sequence
<220> FEATURE:
<223> OTHER INFORMATION: Monoclonal antibody

<400> SEQUENCE: 66

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Thr Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Gly Arg Phe Ser Gly Ser Gly Ser Gly Thr Asp Phe Thr Leu Lys Ile
65                  70                  75                  80

Ser Arg Val Glu Ala Glu Asp Ile Gly Val Tyr Tyr Cys Met Gln Ala
                85                  90                  95

Leu Gln Thr Pro Leu Thr Phe Gly Gln Gly Thr Lys Val Lys Ile Lys
            100                 105                 110

Ala

MONOCLONAL ANTIBODIES THAT NEUTRALIZE ANTHRAX TOXINS

CROSS REFERENCE TO RELATED APPLICATIONS

This application is a divisional of U.S. patent application Ser. No. 14/031,508, filed Sep. 19, 2013, now U.S. Pat. No. 8,961,975, issued Feb. 24, 2015; which is a divisional of U.S. patent application Ser. No. 13/310,463, filed Dec. 2, 2011, now U.S. Pat. No. 8,574,853, issued Nov. 5, 2013; which is a divisional of U.S. patent Ser. No. 12/528,427, filed Aug. 24, 2009, now U.S. Pat. No. 8,071,100, issued Dec. 6, 2011; which is a national stage application under 35 U.S.C. 371 and claims the benefit of International Application No. PCT/US08/54609, having an international filing date of Feb. 21, 2008, which designated the United States; which PCT application claims the benefit of U.S. Provisional Patent Application Ser. No. 60/903,022, entitled "Monoclonal Antibodies that Neutralize Lethal and Edema Factors of Anthrax Toxin" filed Feb. 23, 2007; the contents of each of which are incorporated herein in their entirety by reference.

FIELD OF THE INVENTION

This invention relates generally to the field of immunology and specifically to monoclonal antibodies that bind and/or neutralize anthrax lethal factor (LF) or edema factor (EF).

REFERENCE TO SEQUENCE LISTING, TABLE, OR COMPUTER PROGRAM LISTING

The present application is being filed along with a Sequence Listing in electronic format. The Sequence Listing is provided as a file entitled NIH352.001VPC.txt, created Feb. 21, 2008, which is 36 Kb in size. The information in the electronic format of the Sequence Listing is incorporated herein by reference in its entirety

BACKGROUND OF THE INVENTION

Anthrax is a highly lethal infectious disease caused by the spore-forming bacterium *Bacillus anthracis*. The deliberate distribution of anthrax spores through US mail system in 2001 resulted in 5 deaths among the 11 individuals who contracted inhalational anthrax, which highlight the great threat posed by the potential use of anthrax in terrorism and warfare. The lethality of inhalational anthrax is primarily due to the action of anthrax toxins. Bacterium produces three toxin components; they are protective antigen (PA), lethal factor (LF), and edema factor (EF). PA together with LF forms lethal toxin (LT) and PA together with EF forms edema toxin (ET). PA functions as a vehicle to mediate the cellular uptake of the LF and EF. LF is a zinc-dependent endopeptidase that cleaves mitogen-activated protein kinase kinases (MEKs) and can replicate symptoms of anthrax disease when injected in animals with PA. EF is a calcium-calmodulin-dependent adenylate cyclase with a range of toxic effects in the host. These toxins are the dominant virulence factors for anthrax disease.

Currently there are no approved therapies for anthrax disease except antibiotics. Treatment with antibiotics, though, has considerable limitations. Exposure to the bacterium followed by bacterial division leads to the production of large quantities of the anthrax toxins. Thus, unless exposure is diagnosed early enough for vigorous antibiotic treatment, patients will succumb to disease even after the killing of all bacteria. The current vaccine approved by US Food and Drug Administration is also not effective in protecting newly infected individuals, as it requires repeated administration and at least 4 weeks for development of protective titers. Thus, there is a need for anthrax therapies that immediate neutralize the effects of one or more toxin components.

SUMMARY OF THE INVENTION

Embodiments disclosed herein relate to monoclonal antibodies that bind or neutralize anthrax lethal factor (LF) or edema factor (EF). Some embodiments provide such antibodies, fragments of such antibodies retaining anthrax LF- or EF-binding ability, fully human or humanized antibodies retaining anthrax LF- or EF-binding ability, and pharmaceutical compositions including such antibodies. Further embodiments provide for isolated nucleic acids encoding the antibodies described herein or portions thereof and host cells transformed therewith. Some embodiments also include codon-optimized nucleic acids (e.g., nucleic acids that are codon-optimized for expression in humans) encoding one or more of the antibodies described herein or portions thereof. Additional embodiments provide for prophylactic, therapeutic, and diagnostic methods employing the antibodies and nucleic acids of the invention, alone, in combination with each other, or in combination with antibodies capable of binding to PA.

Some embodiments relate to a substantially pure polypeptide comprising a fully human or humanized chimpanzee monoclonal antibody that binds or neutralizes anthrax lethal factor (LF) or edema factor (EF). In some embodiments, the polypeptide can be a monoclonal antibody that binds the antigen to which monoclonal antibody anti-anthrax LF10E antibody binds. In other embodiments, the polypeptide can be a monoclonal antibody that binds the antigen to which monoclonal antibody anti-anthrax LF11H antibody binds. In additional embodiments, the polypeptide can be a monoclonal antibody that binds the antigen to which monoclonal antibody anti-anthrax EF13D antibody binds.

In some embodiments, the antibody can be an Fd fragment. In other embodiments, the antibody can be an Fab fragment.

In some embodiments, the antibody includes a heavy chain CDR3 region having the amino acid sequence of SEQ ID NO: 7, 23, or 39.

In some embodiments, the antibody includes a heavy chain CDR2 region having the amino acid sequence of SEQ ID NO: 5 (when heavy chain CDR3 region is SEQ ID NO: 7), 21 (when heavy chain CDR3 region is SEQ ID NO: 23), or 37 (when heavy chain CDR3 region is SEQ ID NO: 39).

In some embodiments, the antibody includes a heavy chain CDR1 region having the amino acid sequence of SEQ ID NO: 3 (when heavy chain CDR3 region is SEQ ID NO: 7), 19 (when heavy chain CDR3 region is SEQ ID NO: 23), or 35 (when heavy chain CDR3 region is SEQ ID NO: 39).

In some embodiments, the antibody includes a heavy chain Fd region including the amino acid sequence of SEQ ID NO: 1 (when heavy chain CDR3 region is SEQ ID NO: 7), 17 (when heavy chain CDR3 region is SEQ ID NO: 23), or 33 (when heavy chain CDR3 region is SEQ ID NO: 39).

In some embodiments, the antibody includes a light chain CDR3 region having the amino acid sequence of SEQ ID NO: 15 (when heavy chain CDR3 region is SEQ ID NO: 7), 31 (when heavy chain CDR3 region is SEQ ID NO: 23), or 47 (when heavy chain CDR3 region is SEQ ID NO: 39).

In some embodiments, the antibody includes a light chain CDR2 region having the amino acid sequence of SEQ ID NO: 13 (when heavy chain CDR3 region is SEQ ID NO: 7), 29 (when heavy chain CDR3 region is SEQ ID NO: 23), or 45 (when heavy chain CDR3 region is SEQ ID NO: 39).

In some embodiments, the antibody includes a light chain CDR1 region having the amino acid sequence of SEQ ID NO: 11 (when heavy chain CDR3 region is SEQ ID NO: 7), 27 (when heavy chain CDR3 region is SEQ ID NO: 23) or 43 (when heavy chain CDR3 region is SEQ ID NO: 39).

In some embodiments, the antibody includes a light chain region including the amino acid sequence of SEQ ID NO: 9 (when heavy chain CDR3 region is SEQ ID NO: 7), 25 (when heavy chain CDR3 region is SEQ ID NO: 23), or 41 (when heavy chain CDR3 region is SEQ ID NO: 39).

In some embodiments, the antibody includes a heavy chain Fd region including the CDR amino acid sequences of SEQ ID NO: 1 (when heavy chain CDR3 region is SEQ ID NO: 7), 17 (when heavy chain CDR3 region is SEQ ID NO: 23), or 33 (when heavy chain CDR3 region is SEQ ID NO: 39).

In some embodiments, the antibody includes a light chain region including the CDR amino acid sequences of SEQ ID NO: 9 (when heavy chain CDR3 region is SEQ ID NO: 7), 25 (when heavy chain CDR3 region is SEQ ID NO: 23), or 41 (when heavy chain CDR3 region is SEQ ID NO: 39).

Other embodiments relate to an isolated nucleic acid comprising a nucleotide sequence encoding a polypeptide described herein. In some embodiments, the isolated nucleic acid can be SEQ ID NO: 57, SEQ ID NO: 58, SEQ ID NO: 59, SEQ ID NO: 60, SEQ ID NO: 61, or SEQ ID NO: 62. In additional embodiments, the nucleic acid comprises a vector including a regulatory sequence operably joined to said nucleic acid.

Further embodiments relate to a host cell including a vector comprising a nucleic acid of embodiments disclosed herein.

Some embodiments relate to a substantially pure polypeptide comprising a polypeptide encoded by a nucleotide sequence selected from the group consisting of SEQ ID NO: 57, SEQ ID NO: 58, SEQ ID NO: 59, SEQ ID NO: 60, SEQ ID NO: 61, and SEQ ID NO: 62.

Additional embodiments relate to a pharmaceutical preparation comprising a pharmaceutically acceptable carrier; and a substantially pure polypeptide of embodiments disclosed herein.

More embodiments relate to a diagnostic preparation comprising a pharmaceutically acceptable carrier; and a substantially pure polypeptide of embodiments disclosed herein. Some embodiments relate to a method for the treatment or amelioration of anthrax disease or symptoms thereof comprising administering to a patient a therapeutically effective amount of the pharmaceutical preparation.

Other embodiments relate to a method for prophylaxis against anthrax disease comprising administering to a patient a prophylactically effective amount of the pharmaceutical preparation.

Some embodiments relate to a method for the diagnosis of anthrax disease comprising administering to a patient an effective amount of a diagnostic preparation, and detecting binding of the substantially pure polypeptide as a determination of the presence of anthrax disease.

Further embodiments relate to a method of detecting the presence of anthrax LF or EF in a biological sample comprising contacting said sample with a diagnostic preparation, and assaying binding of the substantially pure polypeptide as a determination of the presence of said anthrax LF or EF.

In some embodiments, the pharmaceutical preparation comprises a polypeptide capable of neutralizing LF. In additional embodiments, the pharmaceutical preparation further comprises a polypeptide capable of neutralizing EF. In yet additional embodiments, the pharmaceutical preparation further comprises a polypeptide capable of neutralizing PA.

BRIEF DESCRIPTION OF THE DRAWINGS

FIGS. 1A and 1B. Alignment of the deduced amino acid sequences of the variable domains of the heavy (FIG. 1A) and kappa (FIG. 1B) chains of anti-LP clones. Substitutions relative to LF9D are shown in single amino acid letters. Identical residues are indicated by dashes. Absence of corresponding residues relative to the longest sequence is indicated by stars. Complementarity-determining regions (CDR1, CDR2, and CDR3) and framework regions (FR1, FR2, FR3, and FR4) are indicated above the sequence alignments. VH LF9D—SEQ ID NO: 49; VH LF10E—SEQ ID NO: 1; VH LF11H—SEQ ID NO: 17; Vκ LF9D—SEQ ID NO: 50; Vκ LF10E—SEQ ID NO: 9; Vκ LF11H—SEQ ID NO: 25.

FIGS. 2A and 2B. Alignment of the deduced amino acid sequences of the variable domains of the heavy (FIG. 2A) and kappa (FIG. 2B) chains of anti-EF clones. Substitutions relative to EF12A are shown in single amino acid letters. Identical residues are indicated by dashes. Absence of corresponding residues relative to the longest sequence is indicated by stars. Complementarity-determining regions (CDR1, CDR2, and CDR3) and framework regions (FR1, FR2, FR3, and FR4) are indicated above the sequence alignments. VH EF12A—SEQ ID NO: 51; VH EF13D—SEQ ID NO: 33; VH EF14H—SEQ ID NO: 52; VH EF15A—SEQ ID NO: 53; Vκ EF12A—SEQ ID NO: 54; Vκ EF13D—SEQ ID NO: 41; Vκ EF14H—SEQ ID NO: 55; Vκ EF15A—SEQ ID NO: 56.

(FIG. 4A) LT (100 ng/ml) was incubated with serial dilutions of each antibody (1 h, 37 C) prior to treatment of RAW264.7 macrophage cells with LT-mAb mixtures for 4 h. Cell viability was assessed by MIT staining and is presented as a percentage of untreated controls. (FIG. 4B) ET (100 ng/ml) was incubated with serial dilutions of antibody (1 h, 37 C) prior to treatment of RAW264.7 macrophage cells with ET-mAb mixture for 1 h and assessment of cAMP production levels.

FIGS. 5A, 5B, 5C and 5D. LF10E and LF11H bind to LFI-25 and prevent LT-mediated MEK cleavage in cells, but do not prevent LF binding to cleaved PA. Purified toxin proteins LF, PA, EF, FP59 or FP119 were loaded on SDS-PAGE gels (2 ng/well as shown in FIG. 5A, and 10 ng/well as shown in FIG. 5B) and probed with LF10E (FIG. 5A) or LF11H (FIG. 5B) for Western blotting. Antibodies were used at 1:500 dilution. As shown in FIG. 5C and FIG. 5D, LT (1 ug/ml) was preincubated with mAbs (100 ug/ml) for 1 h prior to adding LT or LT-mAb mixtures to CHO cells (FIG. 5C) or RAW 264.7 cells FIG. 5(D). Toxins were then allowed to bind to cells for 1 h prior to Western blotting as described in Materials and Methods. Blots were probed with PA polyclonal (1:5000) and an LF monoclonal (1:1000) which cross-reacts with EF (FIG. 5C) or with MEK1 N-terminal antibody (1:5000) (FIG. 5D).

(FIG. 6A) Comparison of left footpad treated with ET (0.5 ug) (top panel) ET (0.5 ug) pre-mixed with anti-EF mAb EF13D (5 ug) (middle panel) and ET pre-mixed with anti-PA mAb W1 (lower panel). As shown in FIG. 6B and FIG. 6C, mAb EF13D (5 ug) and W1 (5 ug) mediated inhibition of footpad edema induced by ET at 0.5 ug ((FIG. 6B), and at 1.0 ug (FIG. 6C). Averages presented are based on n=3 mice per treatment. (FIG. 6D) Systemically pre-administered mAb EF13D (50 ug and 100 ug) inhibition of footpad edema induced by ET (0.25 ug). mAb was injected IV 1 h prior to toxin administration.

BRIEF DESCRIPTION OF THE SEQ ID NOS

Figure 3A:
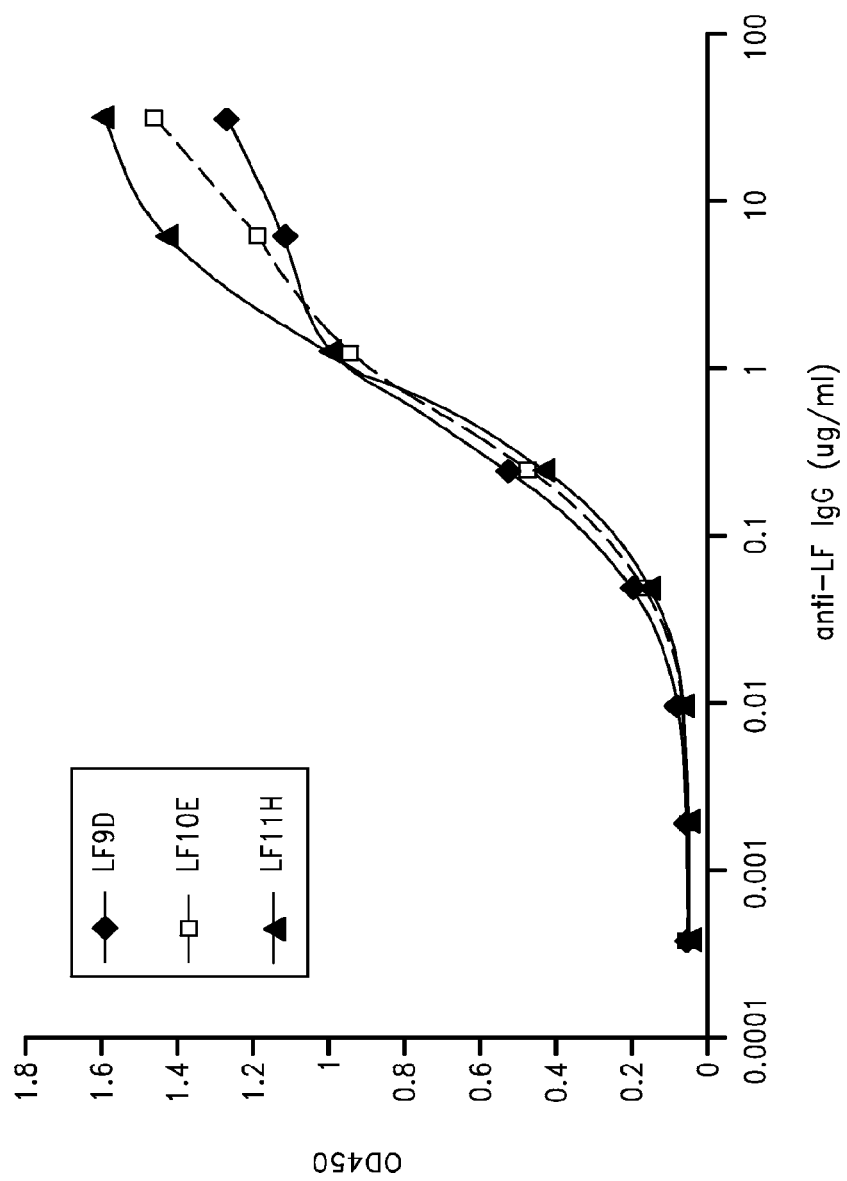
FIGS. 3A and 3B. ELISA titration of anti-LF and anti-EF mAbs. Recombinant LF (FIG. 3A), EF (FIG. 3B), or unrelated proteins (not shown), BSA, thyroglobulin, lysozyme, and phosphorylase-b were used to coat the wells of an ELISA plate. Wells were then incubated with various dilutions of mAbs and bound IgGs were detected by the addition of peroxidase-conjugated anti-human Fc antibody followed by TMB substrate.

| Region | Heavy Chain Anti-LF LF10E Sequence SEQ ID NO: 1 | Light Chain Anti-LF LF10E Sequence SEQ ID NO: 9 |
|---|---|---|
| FR1 | SEQ ID NO: 2 | SEQ ID NO: 10 |
| CDR1 | SEQ ID NO: 3 | SEQ ID NO: 11 |
| FR2 | SEQ ID NO: 4 | SEQ ID NO: 12 |
| CDR2 | SEQ ID NO: 5 | SEQ ID NO: 13 |
| FR3 | SEQ ID NO: 6 | SEQ ID NO: 14 |
| CDR3 | SEQ ID NO: 7 | SEQ ID NO: 15 |
| FR4 | SEQ ID NO: 8 | SEQ ID NO: 16 |

| Region | Heavy Chain Anti-LF LF11H Sequence SEQ ID NO: 17 | Light Chain Anti-LF LF11H Sequence SEQ ID NO: 25 |
|---|---|---|
| FR1 | SEQ ID NO: 18 | SEQ ID NO: 26 |
| CDR1 | SEQ ID NO: 19 | SEQ ID NO: 27 |
| FR2 | SEQ ID NO: 20 | SEQ ID NO: 28 |
| CDR2 | SEQ ID NO: 21 | SEQ ID NO: 29 |
| FR3 | SEQ ID NO: 22 | SEQ ID NO: 30 |
| CDR3 | SEQ ID NO: 23 | SEQ ID NO: 31 |
| FR4 | SEQ ID NO: 24 | SEQ ID NO: 32 |

| Region | Heavy Chain Anti-EF EF13D Sequence SEQ ID NO: 33 | Light Chain Anti-EF EF13D Sequence SEQ ID NO: 41 |
|---|---|---|
| FR1 | SEQ ID NO: 34 | SEQ ID NO: 42 |
| CDR1 | SEQ ID NO: 35 | SEQ ID NO: 43 |
| FR2 | SEQ ID NO: 36 | SEQ ID NO: 44 |
| CDR2 | SEQ ID NO: 37 | SEQ ID NO: 45 |
| FR3 | SEQ ID NO: 38 | SEQ ID NO: 46 |
| CDR3 | SEQ ID NO: 39 | SEQ ID NO: 47 |
| FR4 | SEQ ID NO: 40 | SEQ ID NO: 48 |

Deposit of Biological Material

The following biological material has been deposited in accordance with the terms of the Budapest Treaty with the American Type Culture Collection (ATCC), Manassas, Va., on the date indicated:

| Biological material | Designation No. | Date |
|---|---|---|
| Chimpanzee Anti-Anthrax PAW1 Fab Fragment in pcomb3H Vector | PTA-6293 | Nov. 10, 2004 |

Chimpanzee Anti-Anthrax PAW1 Fab Fragment in pcomb3H Vector was deposited as ATCC Accession No. PTA-6293 on Nov. 10, 2004 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited biological material is not to be construed as a license to practice the invention in contravention of the rights granted under the authority of any government in accordance with its patent laws.

| Biological material | Designation No. | Date |
|---|---|---|
| Chimpanzee Anti-Anthrax PAW2 Fab Fragment in pcomb3H Vector | PTA-6049 | Jun. 4, 2004 |

Chimpanzee Anti-Anthrax PAW2 Fab Fragment in pcomb3H Vector was deposited as ATCC Accession No. PTA-6049 on Jun. 4, 2004 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited biological material is not to be construed as a license to practice the invention in contravention of the rights granted under the authority of any government in accordance with its patent laws.

| Biological material | Designation No. | Date |
|---|---|---|
| Chimpanzee Anti-Anthrax LF10E Fab Fragment in pcomb3H Vector | PTA-8961 | Feb. 21, 2008 |

Chimpanzee Anti-Anthrax LF10E Fab Fragment in pcomb3H Vector was deposited as ATCC Accession No.

PTA-8961 on Feb. 21, 2008 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited biological material is not to be construed as a license to practice the invention in contravention of the rights granted under the authority of any government in accordance with its patent laws.

| Biological material | Designation No. | Date |
| --- | --- | --- |
| Chimpanzee Anti-Anthrax LF11H Fab Fragment in pcomb3H Vector | PTA-8962 | Feb. 21, 2008 |

Chimpanzee Anti-Anthrax LF11H Fab Fragment in pcomb3H Vector was deposited as ATCC Accession No. PTA-8962 on Feb. 21, 2008 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited biological material is not to be construed as a license to practice the invention in contravention of the rights granted under the authority of any government in accordance with its patent laws.

| Biological material | Designation No. | Date |
| --- | --- | --- |
| Chimpanzee Anti-Anthrax EF13D Fab Fragment in pcomb3H Vector | PTA-8963 | Feb. 21, 2008 |

Chimpanzee Anti-Anthrax EF13D Fab Fragment in pcomb3H Vector was deposited as ATCC Accession No. PTA-8963 on Feb. 21, 2008 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14). Availability of the deposited biological material is not to be construed as a license to practice the invention in contravention of the rights granted under the authority of any government in accordance with its patent laws.

DETAILED DESCRIPTION OF THE PREFERRED EMBODIMENT

Passive immunization using monoclonal antibodies from humans or non-human primates represents an attractive alternative for prevention of anthrax. Chimpanzee immunoglobulins are virtually identical to human immunoglobulins and have clinically useful applications (Ehrlich, P. H. et al. 1990 *Hum. Antibodies Hybridomas* 1:23-26; Ehrlich, P. H. et al. 1988 *Clin. Chem.* 34:1681-1688). Monoclonal antibodies to anthrax LF or EF were recovered utilizing a combinatorial cDNA library of antibody genes using phage display and were analyzed for antigen binding specificity. The $V_H$ and $V_L$ sequences and neutralizing activity against the cytotoxicity of the anthrax toxin in vitro and in vivo were analyzed. The anti-LF antibodies described herein include the highest affinity LF monoclonal described to date (LF10E). The antibody LF11H described herein represents a very unique anti-LF antibody. This antibody has low neutralization titer, works less effectively alone in neutralization of LF activity when compared to LF10E or other LF monoclonals, but is vastly enhanced in its ability in combination with sub-protective anti-PA W1 concentrations. The reverse is also true, where the protection seen with anti-PA W1 is enhanced with this antibody at sub-protective doses. Accordingly, antibodies described herein can be particularly useful for treating and/or detecting anthrax when used alone or in combination with other anti-anthrax toxin antibodies.

DEFINITIONS

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only full-length antibody molecules but also fragments of antibody molecules retaining antigen binding ability. Such fragments are also well known in the art and are regularly employed both in vitro and in vivo. In particular, as used herein, the term "antibody" means not only full-length immunoglobulin molecules but also antigen binding active fragments such as the well-known active fragments F(ab')$_2$, Fab, Fv, and Fd. The term "binding agent" refers to an antibody or other polypeptide having the ability to specifically bind to a particular antigen.

As used herein, the term "anthrax" means any disease caused, directly or indirectly, by infection with *Bacillus anthracis*. Inhalation: Initial symptoms may resemble a common cold—sore throat, mild fever, muscle aches and malaise. After several days, the symptoms may progress to severe breathing problems and shock. Inhalation anthrax is usually fatal. Cutaneous: Anthrax infections can occur when the bacterium enters a cut or abrasion on the skin, such as when handling contaminated wool, hides, leather or hair products (especially goat hair) of infected animals. Skin infection begins as a raised itchy bump that resembles an insect bite but within 1-2 days develops into a vesicle and then a painless ulcer, usually 1-3 cm in diameter, with a characteristic black necrotic (dying) area in the center. Lymph glands in the adjacent area may swell. About 20% of untreated cases of cutaneous anthrax will result in death. Gastrointestinal: The intestinal disease form of anthrax may follow the consumption of contaminated meat and is characterized by an acute inflammation of the intestinal tract. Initial signs of nausea, loss of appetite, vomiting, fever are followed by abdominal pain, vomiting of blood, and severe diarrhea. Intestinal anthrax results in death in 25% to 60% of cases.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their hosts cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of embodiments disclosed herein may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein with respect to nucleic acids, the term "isolated" means: (1) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., B-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

Novel Anti-Anthrax Toxin Monoclonal Antibodies

Embodiments herein relate to the isolation and characterization of novel chimpanzee Fab fragments and their humanized monoclonal antibodies that selectively bind anthrax lethal factor (e.g., LF10E and LF11H) or selectively bind anthrax edema factor (e.g., EF13D). Additionally, these new monoclonal antibodies have been shown to neutralize the cytotoxicity of the anthrax toxin. The paratopes of the anti-anthrax Fab fragments associated with the neutralization epitope on the anthrax LF or EF are defined by the amino acid (aa) sequences of the immunoglobulin heavy and light chain V-regions depicted in FIGS. 1 and 2, and, for LF10E, SEQ ID NO: 1 and SEQ ID NO: 9, for LF11H, SEQ ID NO: 17 and SEQ ID NO: 25, and, for EF13D, SEQ ID NO: 33 and SEQ ID NO: 41. The nucleic acid sequences coding for these aa sequences were identified by sequencing the Fab heavy chain and light chain fragments. Due to the degeneracy of the DNA code, the paratope is more properly defined by the derived aa sequences depicted in FIGS. 1 and 2, and, for LF10E, SEQ ID NO: 1 and SEQ ID NO: 9, for LF11H, SEQ ID NO: 17 and SEQ ID NO: 25, and, for EF13D, SEQ ID NO: 33 and SEQ ID NO: 41.

Some embodiments provide the full-length, humanized monoclonal antibody of the anti-anthrax LF10E antibody, the anti-anthrax LF11H antibody, the anti-anthrax EF13D antibody, or other anti-anthrax antibody in isolated form and/or in pharmaceutical preparations. Similarly, as described herein, embodiments provide isolated nucleic acids, host cells transformed with nucleic acids, and pharmaceutical preparations including isolated nucleic acids, encoding the full-length, humanized monoclonal antibody of the anti-anthrax L10E antibody, the anti-anthrax LF11H antibody or other anti-anthrax LF or EF antibody. Finally, some embodiments include methods, as described more fully herein, employing these antibodies and nucleic acids in the in vitro and in vivo diagnosis, prevention and therapy of anthrax disease.

Significantly, as is well-known in the art, only a small portion of an antibody molecule, the paratope, is involved in the binding of the antibody to its epitope (see, in general, Clark, W. R. 1986 *The Experimental Foundations of Modern Immunology* Wiley & Sons, Inc., New York; Roitt, I. 1991 *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of a full-length antibody. Similarly, an antibody from which the Fc region has been enzymatically cleaved, or which has been produced without the Fc region, designated an Fab fragment, retains one of the antigen binding sites of a full-length antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986, supra; Roitt, 1991, supra). In both the heavy chain Fd fragment and the light chain of IgG immunoglobulins, there are four framework regions (FRI through FR4) separated respectively by three complementarity determining regions (CDR1 through CDR3). The CDRs, and in particular the CDR3 regions, and more particularly the heavy chain CDR3, are largely responsible for antibody specificity.

The complete amino acid sequences of the antigen-binding Fab portion of the anti-anthrax LF10E monoclonal antibody as well as the relevant FR and CDR regions are disclosed herein. SEQ ID NO: 1 discloses the amino acid sequence of the Fd fragment of anti-anthrax LF10E. The amino acid sequences of the heavy chain FR1, CDR1, FR2, CDR2, FR3, CDR3 and FR4 regions are disclosed as SEQ ID NO: 2 through SEQ ID NO: 8, respectively. SEQ ID NO: 9 discloses the amino acid sequence of the light chain of anti-anthrax LF10E. The amino acid sequences of the light chain FR1, CDR1, FR2, CDR2, FR3, CDR3 and FR4 regions are disclosed as SEQ ID NO: 10 through SEQ ID NO: 16, respectively. Accordingly, aspects of the invention comprise, consist, or consist essentially of fragments of any one or more of SEQ ID NOS: 1-16 (e.g., at least, greater than, or equal to 10, 15, 20, 25, 30, 35, 40, 45, or 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, or 350 consecutive amino acids of any one or more of SEQ ID NOS: 1-16) or a nucleic acid encoding said fragment (e.g., a nucleic acid encoding at least, greater than, or equal to 10, 15, 20, 25, 30, 35, 40, 45, or 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, or 350 consecutive amino acids of any one or more of SEQ ID NOS: 1-16).

The complete amino acid sequences of the antigen-binding Fab portion of the anti-anthrax LF11H monoclonal antibody as well as the relevant FR and CDR regions are disclosed herein. SEQ ID NO: 17 discloses the amino acid sequence of the Fd fragment of anti-anthrax LF11H. The amino acid sequences of the heavy chain FR1, CDR1, FR2, CDR2, FR3, CDR3 and FR4 regions are disclosed as SEQ ID NO: 18 through SEQ ID NO: 24, respectively. SEQ ID NO: 25 discloses the amino acid sequence of the light chain of anti-anthrax LF11H. The amino acid sequences of the light chain FR1, CDR1, FR2, CDR2, FR3, CDR3 and FR4 regions are disclosed as SEQ ID NO: 26 through SEQ ID NO: 32, respectively. Accordingly, aspects of the invention comprise, consist, or consist essentially of fragments of any one or more of SEQ ID NOS: 1-16 (e.g., at least, greater than, or equal to 10, 15, 20, 25, 30, 35, 40, 45, or 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, or 350 consecutive amino acids of any one or more of SEQ ID NOS: 17-32) or a nucleic acid encoding said fragment (e.g., a nucleic acid encoding at least, greater than, or equal to 10, 15, 20, 25, 30, 35, 40, 45, or 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, or 350 consecutive amino acids of any one or more of SEQ ID NOS: 17-32).

The complete amino acid sequences of the antigen-binding Fab portion of the anti-anthrax EF13D monoclonal antibody as well as the relevant FR and CDR regions are disclosed herein. SEQ ID NO: 33 discloses the amino acid sequence of the Fd fragment of anti-anthrax EF13D. The amino acid sequences of the heavy chain FR1, CDR1, FR2, CDR2, FR3, CDR3 and FR4 regions are disclosed as SEQ ID NO: 34 through SEQ ID NO: 40, respectively. SEQ ID NO: 41 discloses the amino acid sequence of the light chain of anti-anthrax EF13D. The amino acid sequences of the light chain FR1, CDR1, FR2, CDR2, FR3, CDR3 and FR4 regions are disclosed as SEQ ID NO: 42 through SEQ ID NO: 48, respectively. Accordingly, aspects of the invention comprise, consist, or consist essentially of fragments of any one or more of SEQ ID NOS: 1-16 (e.g., at least, greater than, or equal to 10, 15, 20, 25, 30, 35, 40, 45, or 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, or 350 consecutive amino acids of any one or more of SEQ ID NOS: 33-48) or a nucleic acid encoding said fragment (e.g., a nucleic acid encoding at least, greater than, or equal to 10, 15, 20, 25, 30, 35, 40, 45, or 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, or 350 consecutive amino acids of any one or more of SEQ ID NOS: 33-48).

Embodiments disclosed herein include binding agents that can have the following degrees of amino acid sequence homology or identity to the anti-anthrax LF10E antibody, the anti-anthrax LF11H antibody, the anti-anthrax EF13D antibody, or other anti-anthrax antibody, including framework regions and CDRs or fragments thereof, for example: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Candidate binding agents having greater than or equal to 35% homology or identity can be identified by methods known in the art and can be subsequently examined using functional assays, for example, the assays described herein and those known in the art.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of full-length antibodies with antigen-binding ability, are often referred to as "chimeric" antibodies.

Thus, as will be apparent to one of ordinary skill in the art, the some embodiments also provide for F(ab')$_2$, Fab, Fv and Fd fragments of the anti-anthrax LF10E antibody, the anti-anthrax LF11H antibody, the anti-anthrax EF13D antibody, or other anti-anthrax antibody (e.g., an anti-anthrax PA antibody); chimeric antibodies in which the Fc and/or FR and/or CDR1 and/or CDR2 and/or light chain CDR3 regions of the anti-anthrax LF10E antibody, the anti-anthrax LF11H antibody, the anti-anthrax EF13D antibody, or other anti-anthrax antibody, have been replaced by homologous human or non-human sequences; chimeric F(ab')$_2$ fragment antibodies in which the FR and/or CDR1 and/or CDR2 and/or light chain CDR3 regions of t the anti-anthrax LF10E antibody, the anti-anthrax LF11H antibody, the anti-anthrax EF13D antibody, or other anti-anthrax antibody, have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. Thus, those skilled in the art may alter the anti-anthrax LF10E antibody, the anti-anthrax LF11H antibody, the anti-anthrax EF13D antibody, or other anti-anthrax antibody, by the construction of CDR grafted or chimeric antibodies or antibody fragments containing all, or part thereof, of the disclosed heavy and light chain V-region CDR aa sequences (Jones, P. T. et al. 1986 *Nature* 321:522; Verhoeyen, M. et al. 1988 *Science* 39:1534; and Tempest, P. R. et al. 1991 *Bio/Technology* 9:266), without destroying the specificity of the antibodies for their anthrax epitope. Such CDR grafted or chimeric antibodies or antibody fragments can be effective in prevention and treatment of anthrax infection in animals (e.g. cattle) and man.

In some embodiments, the chimeric antibodies are fully human or humanized chimpanzee monoclonal antibodies including at least the heavy chain CDR3 region of the anti-anthrax LF10E antibody, the anti-anthrax LF11H antibody, the anti-anthrax EF13D antibody, or other anti-anthrax antibody. As noted above, such chimeric antibodies may be produced in which some or all of the FR regions of the anti-anthrax LF10E antibody, the anti-anthrax LF11H antibody, the anti-anthrax EF13D antibody, or other anti-anthrax antibody, have been replaced by other homologous human FR regions. In addition, the Fc portions may be replaced so as to produce IgA or IgM as well as IgG antibodies bearing some or all of the CDRs of the anti-anthrax LF10E antibody, the anti-anthrax LF11H antibody, the anti-anthrax EF13D antibody, or other anti-anthrax antibody. Of particular importance is the inclusion of the heavy chain CDR3 region and, to a lesser extent, the other CDRs of the anti-anthrax LF10E antibody, the anti-anthrax LF11H antibody, the anti-anthrax EF13D antibody, or other anti-anthrax antibody. Such fully human or humanized chimpanzee monoclonal antibodies will have particular utility in that they will not evoke an immune response against the antibody itself.

It is also possible, in accordance with some embodiments, to produce chimeric antibodies including non-human sequences. Thus, one may use, for example, murine, ovine, equine, bovine or other mammalian Fc or FR sequences to replace some or all of the Fc or FR regions of the anti-anthrax LF10E antibody, the anti-anthrax LF11H antibody, the anti-anthrax EF13D antibody, or other anti-anthrax antibody. Some of the CDRs may be replaced as well. Again, however, it is preferred that at least the heavy chain CDR3 of the anti-anthrax LF10E antibody, the anti-anthrax LF11H antibody, the anti-anthrax EF13D antibody, or other anti-anthrax antibody, be included in such chimeric antibodies and, to a lesser extent, it is also preferred that some or all of the other CDRs of the anti-anthrax LF10E antibody, the anti-anthrax LF11H antibody, the anti-anthrax EF13D antibody, or other anti-anthrax antibody, be included. Such chimeric antibodies bearing non-human immunoglobulin sequences admixed with the CDRs of the anti-anthrax LF10E antibody, the anti-anthrax LF11H antibody, the anti-anthrax EF13D antibody, or other anti-anthrax antibody, are not preferred for use in humans and are particularly not preferred for extended use because they may evoke an immune response against the non-human sequences. They may, of course, be used for brief periods or in immunosuppressed individuals but, again, fully human or humanized chimpanzee monoclonal antibodies are preferred. Because such antibodies may be used for brief periods or in immunosuppressed subjects, chimeric antibodies bearing non-human mammalian Fc and FR sequences but including at least the heavy chain CDR3 of the anti-anthrax LF10E antibody, the anti-anthrax LF11H antibody, the anti-anthrax EF13D antibody, or other anti-anthrax antibody, are contemplated as alternative embodiments.

For inoculation or prophylactic uses, the antibodies of embodiments disclosed herein are preferably full-length antibody molecules including the Fc region. Such full-length antibodies may have longer half-lives than smaller fragment antibodies (e.g. Fab) and may be more suitable for intravenous, intraperitoneal, intramuscular, intracavity, subcutaneous, or transdermal administration.

In some embodiments, Fab fragments, including chimeric Fab fragments, are preferred. Fabs offer several advantages over F(ab')$_2$ and whole immunoglobulin molecules for this therapeutic modality. First, because Fabs have only one binding site for their cognate antigen, the formation of immune complexes is precluded whereas such complexes can be generated when bivalent F(ab')$_2$ s and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as E. coli, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression mammalian cells in culture with the attendant problems of serum-containing culture medium. In contrast, production of Fabs in E. coli eliminates these difficulties and makes it possible to produce these antibody fragments in large fermenters which are less expensive than cell culture-derived products.

In addition to Fabs, smaller antibody fragments and epitope-binding peptides having binding specificity for the epitope defined by the anti-anthrax LF10E antibody, the anti-anthrax LF11H antibody, the anti-anthrax EF13D antibody, or other anti-anthrax antibody, are also contemplated by some embodiments and can also be used to bind or neutralize the toxin. For example, single chain antibodies can be constructed according to the method of U.S. Pat. No. 4,946,778, to Ladner et al. Single chain antibodies comprise the variable regions of the light and heavy chains joined by a flexible linker moiety. Yet smaller is the antibody fragment known as the single domain antibody or Fd, which comprises an isolated VH single domain. Techniques for obtaining a single domain antibody with at least some of the binding specificity of the full-length antibody from which they are derived are known in the art.

It is possible to determine, without undue experimentation, if an altered or chimeric antibody has the same specificity as the anti-anthrax LF10E antibody, the anti-anthrax LF11H antibody, the anti-anthrax EF13D antibody, or other anti-anthrax antibody of embodiments disclosed herein by ascertaining whether the former blocks the latter from binding to anthrax toxin (e.g., LF, EG, or PA). If the monoclonal antibody being tested competes with the anti-anthrax LF10E antibody, the anti-anthrax LF11H antibody, the anti-anthrax EF13D antibody, or other anti-anthrax antibody, as shown by a decrease in binding of the anti-anthrax LF10E antibody, the anti-anthrax LF11H antibody, the anti-anthrax EF13D antibody, or other anti-anthrax antibody, then it is likely that the two monoclonal antibodies bind to the same, or a closely spaced, epitope. Still another way to determine whether a monoclonal antibody has the specificity of the anti-anthrax LF10E antibody, the anti-anthrax LF11H antibody, the anti-anthrax EF13D antibody, or other anti-anthrax antibody of embodiments disclosed herein is to pre-incubate the anti-anthrax LF10E antibody, the anti-anthrax LF11H antibody, the anti-anthrax EF13D antibody, or other anti-anthrax antibody, with anthrax toxin (e.g., LF for LF10E and LF11H and EF for EF13D) with which it is normally reactive, and then add the monoclonal antibody being tested to determine if the monoclonal antibody being tested is inhibited in its ability to bind anthrax toxin. If the monoclonal antibody being tested is inhibited then, in all likelihood, it has the same, or a functionally equivalent, epitope and specificity as the anti-anthrax LF10E antibody, the anti-anthrax LF11H antibody, the anti-anthrax EF13D antibody, or other anti-anthrax antibody of embodiments disclosed herein. Screening of monoclonal antibodies can be carried out utilizing anthrax toxin and determining whether the monoclonal antibody neutralizes cytotoxicity of the anthrax toxin.

By using the antibodies of embodiments disclosed herein, it is now possible to produce anti-idiotypic antibodies which can be used to screen other monoclonal antibodies to identify whether the antibody has the same binding specificity as an antibody of embodiments disclosed herein. In addition, such antiidiotypic antibodies can be used for active immunization (Herlyn, D. et al. 1986 Science 232:100). Such anti-idiotypic antibodies can be produced using well-known hybridoma techniques (Kohler, G. and Milstein, C. 1975 Nature 256:495). An anti-idiotypic antibody is an antibody which recognizes unique determinants present on the monoclonal antibody produced by the cell line of interest. These determinants are located in the hypervariable region of the antibody. It is this region which binds to a given epitope and, thus, is responsible for the specificity of the antibody.

An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibodies of embodiments disclosed herein, it is possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

Nucleic Acids Encoding Anti-Anthrax Antibodies

Given the disclosure herein of the amino acid sequences of the heavy chain Fd and light chain variable domains of the anti-anthrax LF10E antibody, the anti-anthrax LF11H antibody, the anti-anthrax EF13D antibody, or other anti-anthrax antibody, one of ordinary skill in the art is now enabled to produce nucleic acids, which encode this antibody or which encode the various fragment antibodies or chimeric antibodies described above. It is contemplated that such nucleic acids will be operably joined to other nucleic acids forming a recombinant vector for cloning or for expression of the antibodies of embodiments disclosed herein. Embodiments disclosed herein include any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the immunoglobulin V-regions of the anti-anthrax LF10E antibody, the anti-anthrax LF11H antibody, the anti-anthrax EF13D antibody, or other anti-anthrax antibody, including framework and CDRs or parts thereof, and a suitable promoter either with (Whittle, N. et al. 1987 Protein Eng. 1:499 and Burton, D. R. et al. 1994 Science 266:1024) or without (Marasco, W. A. et al. 1993 PNAS USA 90:7889 and Duan, L. et al. 1994 PNAS USA 91:5075) a signal sequence for export or secretion. Such vectors may be transformed or transfected into prokaryotic (Huse, W. D. et al. 1989 Science 246:1275; Ward, S. et al. 1989 Nature 341:544; Marks, J. D. et al. 1991 J Mol Biol 222:581; and Barbas, C. F. et al. 1991 PNAS USA 88:7987) or eukaryotic (Whittle, N. et al. 1987 Protein Eng 1:499 and Burton, D. R. et al. 1994 Science 266:1024) cells or used for gene therapy (Marasco, W. A. et al. 1993 PNAS USA 90:7889 and Duan, L. et al. 1994 PNAS USA 91:5075) by conventional techniques, known to those with skill in the art.

The expression vectors of embodiments disclosed herein include regulatory sequences operably joined to a nucleotide sequence encoding one of the antibodies of embodiments disclosed herein (e.g., such nucleic acids can be provided by SEQ ID NOS: 57-62). Some embodiments also include fragments of the nucleic acids described herein that encode a functional domain of one or more of the antibodies described herein (e.g., a fragment of SEQ ID NOS: 57-62 that comprise, consist, or consist essentially of at least, greater than, or equal to 10, 20, 30, 40, 50, or 60, 70, 80, 90, 100, 150, 200, 250, 300, 350, 400, 450, 500, 550, 600, 650, 700, 750, 800, 850, 900, 950, 1000, 1050, or 1100 consecutive nucleotides). As used herein, the term "regulatory sequences" means nucleotide sequences which are necessary for or conducive to the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the antibodies may be accomplished by any of a variety of standard means known in the art.

Embodiments disclosed herein include nucleic acids encoding binding agents that can have the following degrees of nucleotide sequence homology or identity to nucleic acids encoding anti-anthrax LF10E antibody, the anti-anthrax LF11H antibody, the anti-anthrax EF13D antibody, or other anti-anthrax antibody, including framework regions and CDRs or fragments thereof, for example: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Candidate binding agents having greater than or equal to 35% homology or identity can be identified by methods known in the art and can be subsequently examined using functional assays, for example, the assays described herein and those known in the art.

A preferred vector for screening monoclonal antibodies, but not necessarily preferred for the mass production of the antibodies of embodiments disclosed herein, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of embodiments disclosed herein, and, optionally, (3) a fusion protein domain. The vector includes DNA regulatory sequences for expressing the fusion polypeptide, preferably prokaryotic, regulatory sequences. Such vectors can be constructed by those with skill in the art and have been described by Smith, G. P. et al. (1985 *Science* 228:1315; Clackson, T. et al. 1991 *Nature* 352:624; Kang et al. 1991 in: *Methods: A Companion to Methods in Enzymology: Vol.* 2, R. A. Lerner and D. R. Burton, eds. Academic Press, NY, pp 111-118; Barbas, C. F. et al. 1991 *PNAS USA* 88:7978; Roberts, B. L. et al. 1992 *PNAS USA* 89:2429).

A fusion polypeptide may be useful for purification of the antibodies of embodiments disclosed herein. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein to the membrane of the host cell, such as the periplasmic membrane of Gram-negative bacteria. A preferred secretion signal for *E. coli* is a pelB secretion signal. The leader sequence of the pelB protein has previously been used as a secretion signal for fusion proteins (Better, M. et al. 1988 *Science* 240:1041; Sastry, L. et al. 1989 *PNAS USA* 86:5728; and Mullinax, R. L. et al., 1990 *PNAS USA* 87:8095). Amino acid residue sequences for other useful secretion signal polypeptide domains from *E. coli* be found in Neidhard, F. C. (ed.), 1987 *Escherichia coli and Salmonella Typhimurium: Typhimurium Cellular and Molecular Biology*, American Society for Microbiology, Washington, D.C.

To achieve high levels of gene expression in *E. coli*, it may be necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine et al. 1975 *Nature* 254:34). The sequence, which is called the Shine-Dalgarno (SD) sequence, is complementary to the 3' end of *E. coli* 16S rRNA. Binding of the ribosome to mRNA and the sequence at the 3' end of the mRNA can be affected by several factors: the degree of complementarity between the SD sequence and 3' end of the 16S rRNA; the spacing lying between the SD sequence and the AUG; and the nucleotide sequence following the AUG, which affects ribosome binding. The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColEI found in pBR322 and a variety of other common plasmids. Also preferred is the p15A origin of replication found on pACYC and its derivatives. The ColEI and p15A replicons have been extensively utilized in molecular biology, are available on a variety of plasmids and are described by Sambrook. et al. 1989 *Molecular Cloning: A Laboratory Manual,* 2nd edition, Cold Spring Harbor Laboratory Press.

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as those commercially available from suppliers such as Invitrogen, (San Diego, Calif.).

When the antibodies include both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the full-length antibodies of embodiments disclosed herein or the F(ab')$_2$, Fab or Fv fragment antibodies of embodiments disclosed herein, refers to a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a di-cistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

Antibodies may additionally be produced by eukaryotic cells such as CHO cells, human or mouse hybridomas, immortalized B-lymphoblastoid cells, and the like. In this case, a vector is constructed in which eukaryotic regulatory sequences are operably joined to the nucleotide sequences encoding the antibody polypeptide or polypeptides. The design and selection of an appropriate eukaryotic vector is within the ability and discretion of one of ordinary skill in the art. The subsequent purification of the antibodies may be accomplished by any of a variety of standard means known in the art.

Antibodies may furthermore be produced in plants. In 1989, Hiatt et al. (1989 *Nature* 342:76) first demonstrated that functional antibodies could be produced in transgenic plants. Since then, a considerable amount of effort has been invested in developing plants for antibody (or "plantibody") production (for reviews see Giddings G. et al. 2000 *Nat Biotechnol* 18:1151; Fischer R. and Emans N. 2000 *Transgenic Res* 9:279). Recombinant antibodies can be targeted to seeds, tubers, or fruits, making administration of antibodies in such plant tissues advantageous for immunization programs in developing countries and worldwide.

Other embodiments provide host cells, both prokaryotic and eukaryotic, transformed or transfected with, and therefore including, the vectors of the present invention.

Diagnostic and Pharmaceutical Anti-Anthrax Antibody Preparations

Some embodiments also relate to methods for preparing diagnostic or pharmaceutical compositions comprising the monoclonal antibodies of embodiments disclosed herein or polynucleotide sequences encoding the antibodies of embodiments disclosed herein or part thereof, the pharmaceutical compositions being used for immunoprophylaxis or immunotherapy of anthrax disease. The pharmaceutical preparation includes a pharmaceutically acceptable carrier. Such carriers, as used herein, means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Additional embodiments relate to monoclonal antibodies whose heavy chains comprise in CDR3 the polypeptide having SEQ ID NO: 7, and/or whose light chains comprise in CDR3 the polypeptide having SEQ ID NO: 15; whose heavy chains comprise in CDR3 the polypeptide having SEQ ID NO: 23, and/or whose light chains comprise in CDR3 the polypeptide having SEQ ID NO: 31; whose heavy chains comprise in CDR3 the polypeptide having SEQ ID NO: 39, and/or whose light chains comprise in CDR3 the polypeptide having SEQ ID NO: 47; and conservative variations of these peptides. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also bind or neutralize anthrax LF, EF or PA. Analogously, other embodiments relate to polynucleotides which encode the above noted heavy chain polypeptides and to polynucleotide sequences which are complementary to these polynucleotide sequences. Complementary polynucleotide sequences include those sequences that hybridize to the polynucleotide sequences of embodiments disclosed herein under stringent hybridization conditions.

Antibodies may be labeled by a variety of means for use in diagnostic and/or pharmaceutical applications. There are many different labels and methods of labeling known to those of ordinary skill in the art. Examples of the types of labels which can be used include enzymes, radioisotopes, fluorescent compounds, colloidal metals, chemiluminescent compounds, and bioluminescent compounds. Those of ordinary skill in the art will know of other suitable labels for binding to the monoclonal antibodies of embodiments disclosed herein, or will be able to ascertain such, using routine experimentation. Furthermore, the binding of these labels to the monoclonal antibodies of embodiments disclosed herein can be done using standard techniques common to those of ordinary skill in the art.

Another labeling technique which may result in greater sensitivity consists of coupling the antibodies to low molecular weight haptens. These haptens can then be specifically altered by means of a second reaction. For example, it is common to use haptens such as biotin, which reacts with avidin, or dinitrophenol, pyridoxal, or fluorescein, which can react with specific antihapten antibodies.

The materials for use in the assay of embodiments disclosed herein are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a monoclonal antibody of embodiments disclosed herein that is, or can be, detectably labeled. The kit may also have containers containing buffer(s) and/or a container comprising a reporter-means, such as a biotin-binding protein, such as avidin or streptavidin, bound to a reporter molecule, such as an enzymatic or fluorescent label.

In Vitro Detection and Diagnostics

Monoclonal antibodies of embodiments disclosed herein can be used in vitro, for example, in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies of embodiments disclosed herein are competitive and non-competitive immunoassays in either a direct or indirect format. Examples of such immunoassays include the radioimmunoassay (RIA) and the sandwich (immunometric) assay. Detection of antigens using monoclonal antibodies can be done utilizing immunoassays which are run in either the forward, reverse, or simultaneous modes, including immunohistochemical assays on physiological samples. Those of skill in the art will know, or can readily discern, other immunoassay formats without undue experimentation.

Monoclonal antibodies of embodiments disclosed herein can be bound to many different carriers and used to detect the presence of anthrax PA, LF, and/or EF. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers for binding monoclonal antibodies, or will be able to ascertain such, using routine experimentation.

In some embodiments, anthrax toxins may be detected by the monoclonal antibodies of embodiments disclosed herein when present in biological fluids and tissues. Any sample containing a detectable amount of anthrax LF, EF or PA can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

In Vivo Detection of Anthrax LF, EF, and/or PA

In using the monoclonal antibodies of embodiments disclosed herein for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having anthrax LF, EF or PA for which the monoclonal antibodies are specific.

The concentration of detectably labeled monoclonal antibody which is administered should be sufficient such that the binding to anthrax LF, EF and/or PA is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.01 mg/kg to about 50 mg/kg, preferably 0.1 mg/kg to about 20 mg/kg, most preferably about 0.1 mg/kg to about 2 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions are the bifunctional chelating agents such as diethylenetriaminepentacetic acid (DTPA) and ethylenediaminetetra-acetic acid (EDTA) and similar molecules. Typical examples of metallic ions which can be bound to the monoclonal antibodies include $^{111}$In, $^{97}$Ru, $^{67}$Ga, $^{68}$Ga, $^{72}$As, $^{89}$Zr and $^{201}$Tl.

Monoclonal antibodies can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

The monoclonal antibodies of embodiments disclosed herein can be used in vitro and in vivo to monitor the course of anthrax disease therapy. Thus, for example, by measuring the increase or decrease in the number of cells infected with anthrax or changes in the concentration of anthrax LF, EF, and/or PA present in the body or in various body fluids, it would be possible to determine whether a particular therapeutic regimen aimed at ameliorating anthrax disease is effective.

Prophylaxis and Therapy of Anthrax Disease

The monoclonal antibodies can also be used in prophylaxis and as therapy for anthrax disease in humans. The terms, "prophylaxis" and "therapy" as used herein in conjunction with the monoclonal antibodies of embodiments disclosed herein denote both prophylactic as well as therapeutic administration and both passive immunization with substantially purified polypeptide products, as well as gene therapy by transfer of polynucleotide sequences encoding the product or part thereof. Thus, the monoclonal antibodies can be administered to high-risk subjects in order to lessen the likelihood and/or severity of anthrax disease or administered to subjects already evidencing active anthrax infection. In some embodiments, Fab fragments can also bind or neutralize anthrax LF, EF, and/or PA and therefore may be used to treat anthrax infection.

In some contexts, a "prophylactically effective amount" of monoclonal antibodies refers to a dosage large enough to produce the desired effect in the protection of individuals against anthrax infection for a reasonable period of time, such as one to two months or longer following administration. A prophylactically effective amount is not, however, a dosage so large as to cause adverse side effects, such as hyperviscosity syndromes, pulmonary edema, congestive heart failure, and the like. Generally, a prophylactically effective amount may vary with the subject's age, condition, and sex, as well as the extent of the disease in the subject and can be determined by one of skill in the art. The dosage of the prophylactically effective amount may be adjusted by the individual physician or veterinarian in the event of any complication. A prophylactically effective amount may vary from about 0.01 mg/kg to about 50 mg/kg, preferably from about 0.1 mg/kg to about 20 mg/kg, most preferably from about 0.2 mg/kg to about 2 mg/kg, in one or more administrations (priming and boosting).

In some contexts, a "therapeutically effective amount" of monoclonal antibodies of refers to a dosage large enough to produce the desired effect in which the symptoms of anthrax disease are ameliorated or the likelihood of infection is decreased. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the disease in the subject and can be determined by one of skill in the art. The dosage of the therapeutically effective amount may be adjusted by the individual physician or veterinarian in the event of any complication. A therapeutically effective amount may vary from about 0.01 mg/kg to about 50 mg/kg, preferably from about 0.1 mg/kg to about 20 mg/kg, most preferably from about 0.2 mg/kg to about 2 mg/kg, in one or more dose administrations daily, for one or several days. Preferred is administration of the antibody for 2 to 5 or more consecutive days in order to avoid "rebound" of bacterial replication from occurring.

Monoclonal antibodies can be administered by injection or by gradual infusion over time. The administration of monoclonal antibodies of the invention may, for example, be intravenous, intraperitoneal, intramuscular, intracavity, subcutaneous, or transdermal. Techniques for preparing injectate or infusate delivery systems containing antibodies are well known to those of skill in the art. Generally, such systems should utilize components which will not significantly impair the biological properties of the antibodies, such as the paratope binding capacity (see, for example, *Remington's Pharmaceutical Sciences, 18th edition,* 1990, Mack Publishing). Those of skill in the art can readily determine the various parameters and conditions for producing antibody injectates or infusates without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and the like.

In some embodiments, monoclonal antibodies disclosed herein may be used individually or in combination with other antibodies in detection, prophylaxis and/or as therapy for anthrax disease in humans. For example, a cocktail of neutralizing antibodies against all three components (PA, LF, and EF) of anthrax toxin can be used in detection, prophylaxis and/or as therapy. Alternatively, pair-wise combinations can be used. For example, a therapy may include anti-PA antibodies and anti-LF antibodies; anti-PA and anti-EF antibodies; or anti-LF and anti-EF antibodies. Anti-PA antibodies that may be used in embodiments disclosed herein include, but is not limited to, those described in PCT Publication No. WO2007/084107, which is herein incorporated by reference in its entirety.

The following example provides greater discussion of the manufacture and characterization of the anthrax neutralizing embodiments described above.

Example 1

Anthrax is a highly lethal infectious disease caused by the spore-forming bacterium *Bacillus anthracis*. The deliberate distribution of anthrax spores through US mail system in 2001 resulted in 5 deaths among the 11 individuals who contracted inhalational anthrax (Jernigan, J. A. et al. 2001 *Emerg. Infect. Dis.* 7:933-944), which highlight the great threat posed by the potential use of anthrax in terrorism and warfare. The lethality of inhalational anthrax is primarily due to the action of anthrax toxins. Bacterium produces three toxin components; they are protective antigen (PA), lethal factor (LF), and edema factor (EF). PA together with LF forms lethal toxin (LT) and PA together with EF forms edema toxin (ET). PA functions as a vehicle to mediate the cellular uptake of the LF and EF (for review see Young, J. A. et al. 2007 *Annu. Rev. Biochem.*). LF is a zinc-dependent endopeptidase that cleaves mitogen-activated protein kinase kinases (MEKs) (Duesbery, N. S. et al. 1998 *Science* 280: 734-737; Pellizzari, R. et al. *FEBS Lett.* 462:199-204; Vitale, G. et al. 1998 *Biochem. Biophys. Res. Commun.* 248:706-711) and can replicate symptoms of anthrax disease when injected in animals with PA (Moayeri, M. et al. 2004 *Curr. Opin. Microbiol.* 7:19-24). EF is a calcium-calmodulin-dependent adenylate cyclase with a range of toxic effects in the host (Firoved, A. M. et al. 2005 *Am. J. Pathol.* 167: 1309-1320; Leppla, S. H. 1982 *Proc. Natl. Acad. Sci. U.S.A* 79:3162-3166). These toxins are the dominant virulence factors for anthrax disease.

Currently there are no approved therapies for anthrax disease except antibiotics. Although antibiotics are effective, they have limitations. Exposure to the bacterium followed by bacterial division leads to production of large quantities of the anthrax toxins. Thus, unless exposure is diagnosed early enough for vigorous antibiotic treatment, patients will succumb to disease even after the killing of all bacteria. The current vaccine approved by US Food and Drug Administration is also not effective in protecting newly infected individuals, as it requires repeated administration and at least 4 weeks for development of protective titers. Thus, in the absence of any small molecule toxin inhibitors, monoclonal antibodies against toxin components are viable candidates for immediate neutralization of the effects of toxin. Although protective antigen (PA) has been a primary target for passive protection (Chen, Z. et al. 2006 *J. Infect. Dis.* 193:625-633; Maynard, J. A. et al. 2002 *Nat. Biotechnol.* 20:597-601; Peterson, J. W. et al. 2007 *Infect. Immun.* 75:3414-3424; Sawada-Hirai, R. et al. 2004 *J. Immune. Based. Ther. Vaccines.* 2:5; Vitale, L. et al. 2006 *Infect. Immun.* 74:5840-5847; Wild, M. A. et al. 2003 *Nat. Biotechnol.* 21:1305-1306) it has been suggested that lethal factor (LF) and edema factor (EF) also play an important role in providing immunity (Galloway, D. 2004 *Vaccine* 22:1604-1608; Pezard, C. et al. 1995 *Infect. Immun.* 63:1369-1372; Price, B. M. et al. 2001 *Infect. Immun.* 69:4509-4515) and thus may represent alternative targets for monoclonal antibody therapy against anthrax. Synergistic effect on protective efficacy by combinatorial treatment with anti-PA and anti-LF antibodies has also been demonstrated (Brossier, F. et al. 2004. *Infect. Immun.* 72:6313-6317). Furtheremore, there are concerns that PA may be mutated within currently known mAb neutralizing epitopes such that anti-PA therapies are no longer effective against this toxin. A cocktail of more than one mAbs able to recognize distinct epitopes on multiple toxin proteins (PA, LF or EF) is contemplated to broaden the spectrum of protection against anthrax. In recent years, several anti-LF neutralizing mAbs have been reported (Lim, N. K. 2005 *Infect. Immun.* 73:6547-6551; Little, S. F. et al. 1990 *Infect. Immun.* 58:1606-1613; Zhao, P. et al. 2003 *Hum. Antibodies* 12:129-135). However, there have been no reports on anti-EF neutralizing mAbs. A single report of an anti-LF mAb cross-reactive with EF did not show anti-EF neutralizing function (Little, S. F. et al. 1990 *Infect. Immun.* 58:1606-1613).

Chimpanzee immunoglobulins are virtually identical to human immunoglobulins and have clinically useful applications (Ehrlich, P. H. et al. 1990 *Hum. Antibodies Hybridomas* 1:23-26; Ehrlich, P. H. et al. 1988 *Clin. Chem.* 34:1681-1688). Chimpanzee mAbs were developed that were specific to LF or EF. A combinatorial cDNA library of antibody genes using phage display was utilized to isolate three anti-LF and four anti-EF Fab clones. The neutralizing ability of two LF mAbs and one EF mAb in vitro and in vivo are described and analyses of their mechanism of function are presented. The anti-EF antibody EF13D described in this publication is the first report of a neutralizing antibody against EF.

Isolation of LF and EF-Specific Fabs and Sequence Analysis.

Figure 3B:
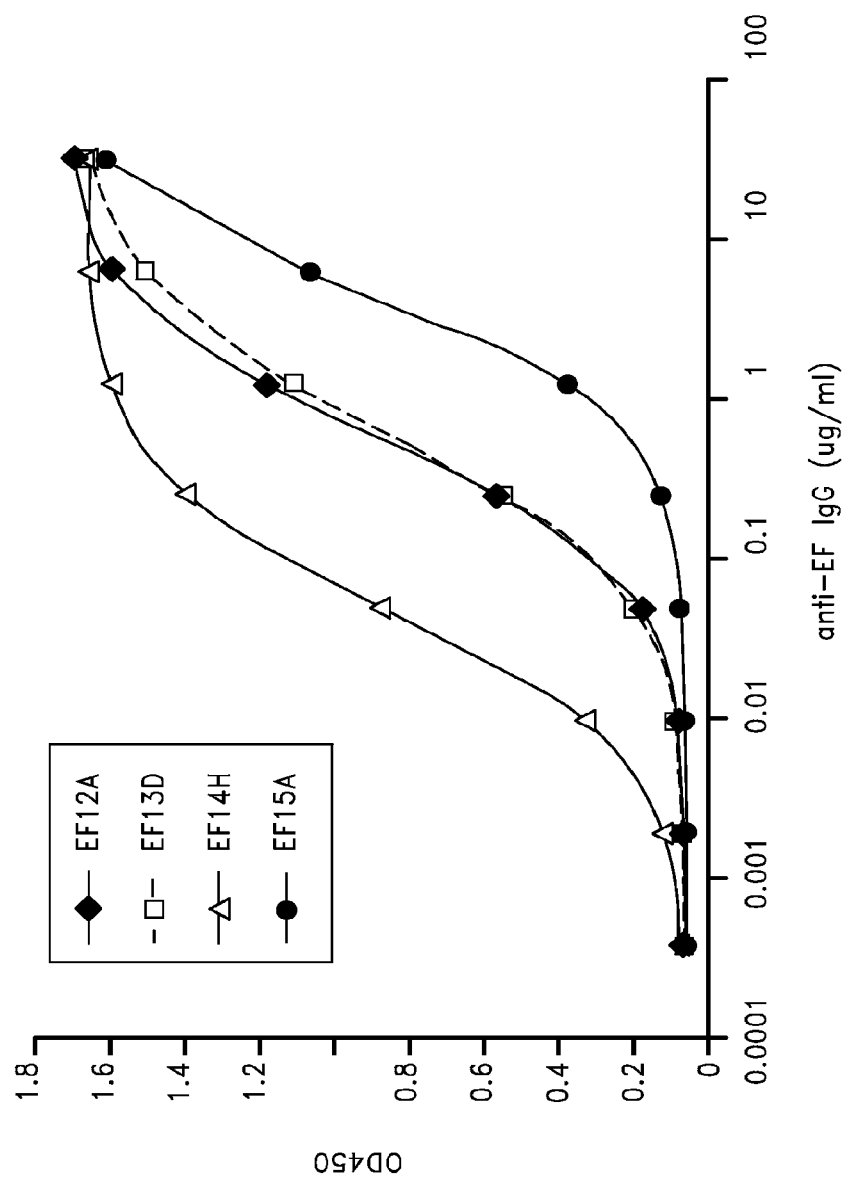

Following three rounds of panning against LF or EF, 96 individual clones were screened for binding to the toxins by phage ELISA and BSA coated plate was used for negative control. Ninety two clones preferentially bound to LF, but not to BSA while all 96 clones bound to EF. Sequence analysis identified three unique anti-LF Fab clones and four unique anti EF clones with distinct VH and VK sequences (FIGS. 1 and 2). These were named as LF9D, LF10E and LF11H and EF12A, EF13D, EF14D and EF15A. The closest human V-gene germline origins of the three isolated clones were assigned by conducting sequence similarity search of all the known human Immunoglobulin genes (Tables 1, 2). The clones were examined for their binding specificity by ELISA. All clones preferentially bound their target toxin (FIGS. 3A and 3B) with no binding to the unrelated proteins ([BSA], thyroglobulin, lysozyme, and phosphorylase b).

TABLE 1

Assignment of Three Chimpanzee anti-LF Fab Clones to Their Closest Human Germline Courtparts Based on Nucleotide Sequence Homology

| | | Germline gene in:[a] | | | | | |
|---|---|---|---|---|---|---|---|
| | VH | Segment | | | Vκ | Segment | |
| MAb | Family | VH | D | JH | Family | Vκ | Jκ |
| LF9D | 3 | DP-47 | D3 | J5b | I | DPK8 | J4 |
| LF10E | 3 | DP-47 | D5-12 | J4b | I | DPK3 | J4 |
| LF11H | 5 | D7-73 | D7-27 | J6c | I | DPK3 | J1 |

[a] The closest human V-gene germlines were identified by search on the V-base database.

TABLE 2

Assignment of Four Chimpanzee anti-EF Fab Clones to Their Closest Human Germline Courtparts Based on Nucleotide Sequence Homology

| | | Germline gene in:[a] | | | | | |
|---|---|---|---|---|---|---|---|
| | VH | Segment | | | Vκ | Segment | |
| MAb | Family | VH | D | JH | Family | Vκ | Jκ |
| EF12A | 3 | DP-85 | D1-26 | J4b | III | Vg/38K | J3 |
| EF13D | 1 | DP-10 | D7-27 | J4b | I | DPK9 | J4 |

TABLE 2-continued

Assignment of Four Chimpanzee anti-EF Fab Clones to Their Closest Human Germline Courtparts Based on Nucleotide Sequence Homology

| | | Germline gene in:[a] | | | | | |
|---|---|---|---|---|---|---|---|
| | VH | Segment | | | Vκ | Segment | |
| MAb | Family | VH | D | JH | Family | Vκ | Jκ |
| EF14H | 3 | LSG12.1 | D4-23 | J6c | I | DPK4 | J3 |
| EF15A | 3 | DP49 | D3-9 | J4b | I | HK137 | J1 |

[a] The closest human V-gene germlines were identified by search on the V-base database.

Figure 4A:
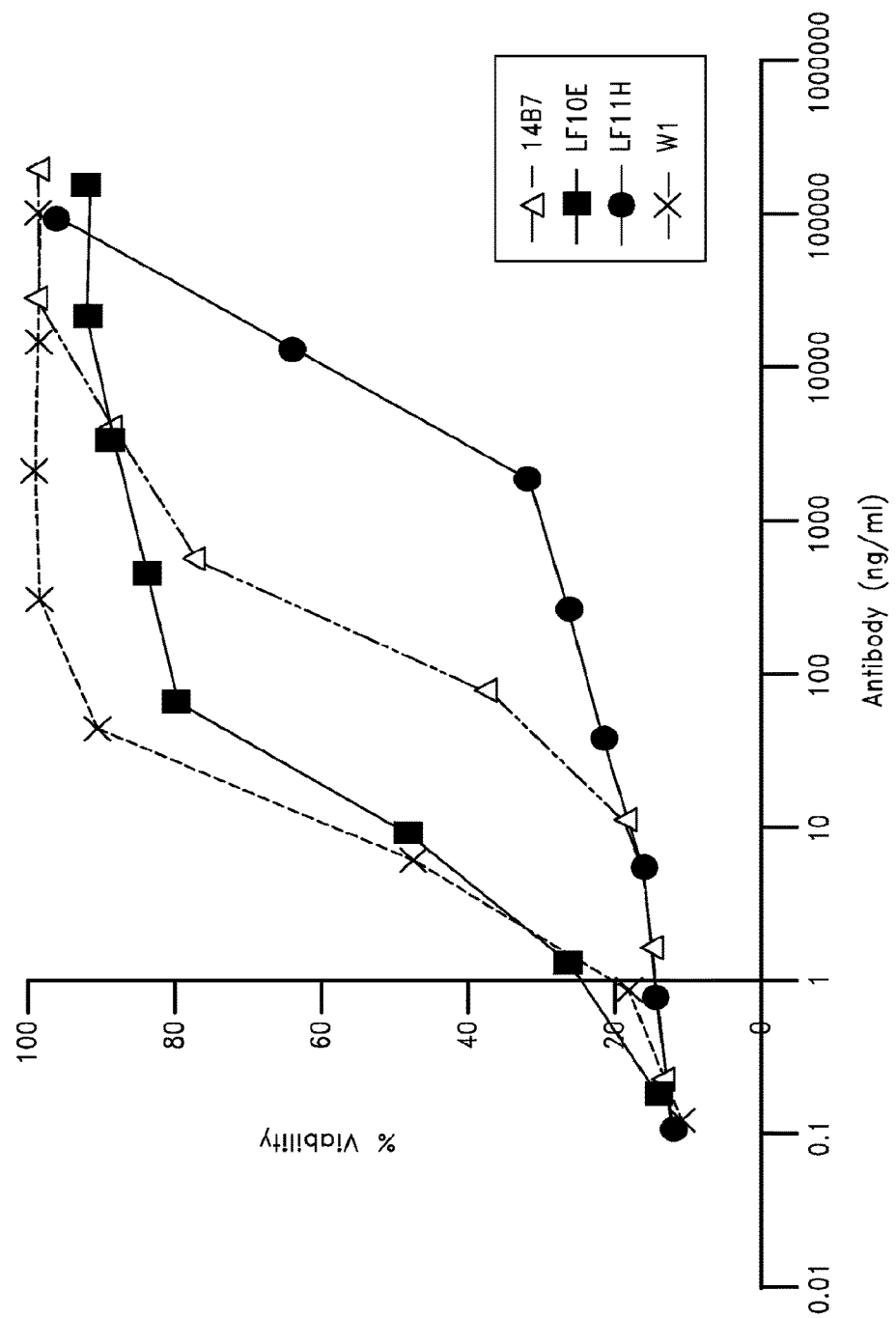
FIGS. 4A and 4B. LF10E and LF11H neutralize LT toxicity and EF13D inhibits ET-mediated cAMP production in cells.

Anti-LF Antibodies LF10E and LF11H Neutralize LT:

The anti-LF mAbs were tested in the standard macrophage toxicity neutralization assays used for assessing anti-PA and anti-LF agents and the EC50s of neutralization for these antibodies were compared to the well characterized monoclonal anti-PA mAbs 14B7 and W1 (FIG. 4A). LF10E protected macrophages with an average EC50 of 15.6±7.5 ng/ml, comparable to the well characterized highly potent W1 anti-PA monoclonal (Chen, Z. et al. 2006 *J. Infect. Dis.* 193:625-633), and was ten-fold more potent than mAb 14B7. LF11H had a much higher EC50 of 62,568±28,331. The affinity of the two neutralizing clones, LF10E and LF11H, were determined by surface plasma resonance and summarized in Table 3.

TABLE 3

Binding affinities of anti-LF MAbs

| MAbs | $k_{on}$ (M$^{-1}$s$^{-1}$) | $k_{off}$(s$^{-1}$) | $K_d$ (nM) |
|---|---|---|---|
| LF10E11 | $2.7 \times 10^5$ | $1.9 \times 10^{-4}$ | 0.69 |
| LF11H10 | $1.3 \times 10^5$ | $1.0 \times 10^{-3}$ | 7.4 |

Recombinant LF was immobilized on the surface of the plasmon resonance sensor chip CM3 by standard NHS/EDC amine coupling method. The Fabs binding responses to LF-protein were collected at a range of concentrations between 0.4 and 2000 nM. The kinetic and equilibrium constants were determined by modeling the surface binding kinetics as a distribution of rate and affinity constants. The standard regularization was extended to incorporate Bayesian expectations that the distribution conforms best to a single site model.

Figure 4B:
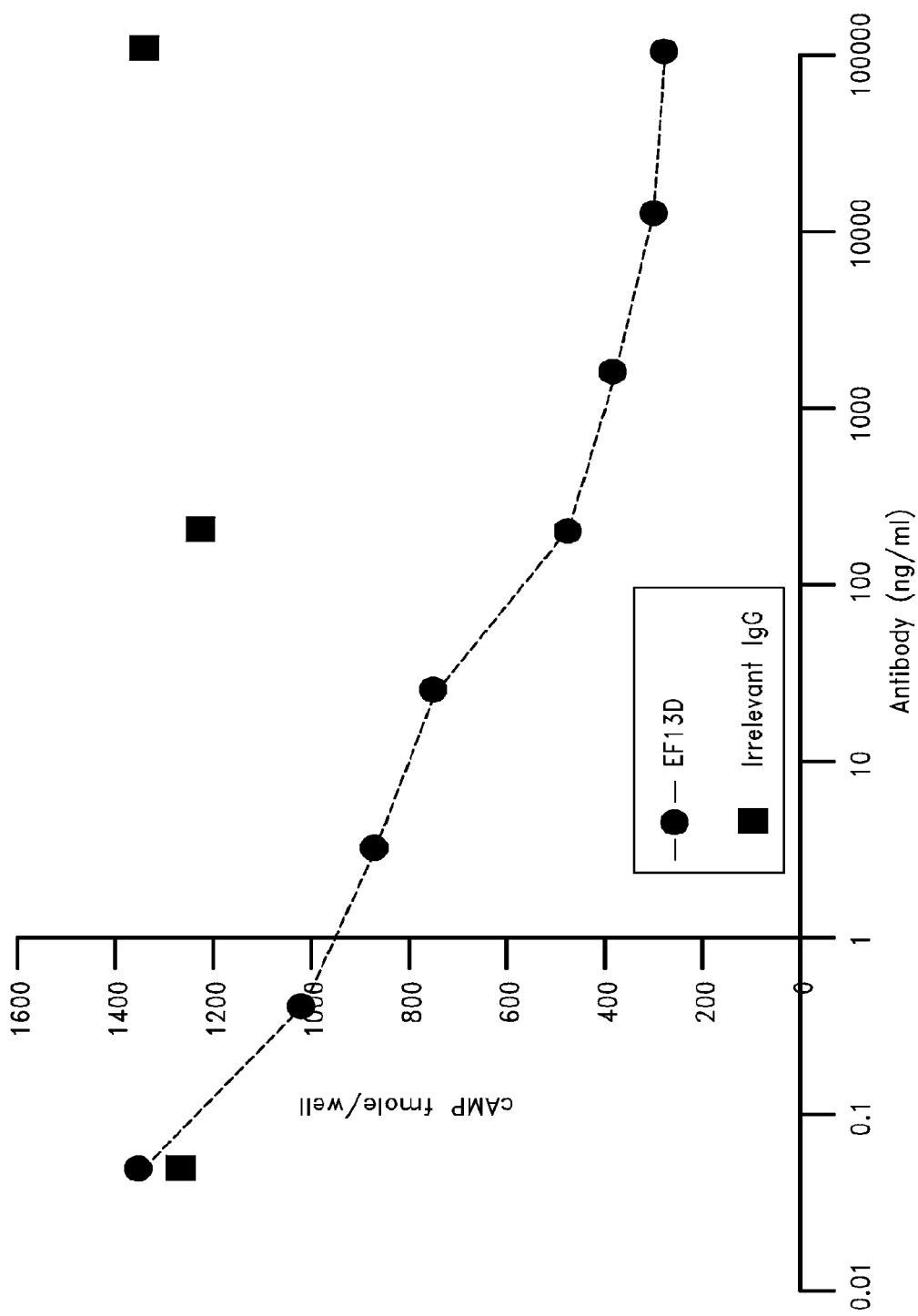

Anti-EF Antibody EF13D Inhibits ET-Mediated cAMP Production in Cells:

Of all the anti-EF mAbs tested for neutralization of ET activity, only a single antibody, EF13D, was able to inhibit ET-mediated cAMP production in RAW264.7 cells (average EC50 of 28 ng/ml) (FIG. 4B). The affinity of this neutralizing clone was measured by surface plasma resonance. The dissociation equilibrium constant (Kd) was determined to be $9.7 \times 10^{-9}$ M with on-rate of $4.12 \times 10^4$ M$^{-1}$s$^{-1}$ and off-rate of $4 \times 10^{-4}$ s$^{-1}$.

LF10E and LF11H Bind to LF1-25 and Prevent LT-Mediated MEK Cleavage in Cells, but do not Prevent LF Binding to Cleaved PA:

To determine the region of LF to which LF10E and LF11H bind, the reactivity of these mAbs was tested with LF and a fusion of the first 254 amino acids of LF with *Pseudomonas aueroginosa* Exotoxin A (FP59) on Western blots. Purified PA, EF and a fusion of the N-terminal region of EF (1-260) to diphtheria toxin (FP119) were used as negative controls. This region of EF has very high homology to LF1-254 and all available polyclonal antibodies to LF cross reacted with EF through binding to this domain. Both mAb LF10E and LF11H bound only to LF and FP59, and had no cross reactivity with EF (FIGS. 5A and 5B). Thus, the epitope for LF10E and LF11H lies in the LF1-254 region, which has previously been shown to be the PA binding domain (Milne, J. C. et al. 1995 *Mol. Microbiol.* 15:661-666). Similar Westerns were performed with anti-EF mAb EF13D and did not show any binding to the EF1-260 domain of FP119, indicating the epitope for mAb EF13D was in the C-terminal region of EF. To test if the anti-LF mAbs reacting with the PA-binding N-terminal LF1-254 domain were interfering with the binding of LF to cell surface cleaved PA through blocking of this domain, LF was incubated with a 100-fold per weight excess of each antibody or with PBS for 1 h prior to adding these mixtures to CHO cells. Similarly, anti-EF mAb EF13D was pre-incubated with ET prior to addition to cells to see if this mAb had any effect on LF binding. As shown in FIG. 5C, none of the mAbs had any effect on the binding of PA to cells or its cleavage to the active PA63 form. Anti-EF mAb EF13D did not inhibit binding of EF to cells, and it was discovered that the LF10E and LF11H did not inhibit LF association with the PA63 on cells. LF was found in equivalent amounts in lysates from cells treated with LT alone, or with LF pre-bound with both antibodies (FIG. 5C). However both antibodies clearly inhibited LF-mediated MEK cleavage in the cytosol (FIG. 5D). This suggests the anti-LF mAbs are unique in that they act at a step subsequent to LF binding to PA but prior to LF delivery to the cytosol.

LF10E and LF11H Protect Rats from LT Toxicity:

The mAbs were next tested for protection in the classic Fischer rat model for LT toxicity. mAbs were pre-mixed in different molar ratios with LT (10 ug/rat), starting with equimolar amounts of antibody and toxin, and reducing antibody to sub-molar concentration relative to toxin. In similar experiments, it was previously established that anti-PA mAb W1 was able to protect rats even at 1:4 (Ab:PA) molar ratio but not at lower concentrations. It was determined that mAb LF10E protected 100% of rats at 1:2 (Ab:LF) ratio but not at lower concentrations, and LF11H only did so at equimolar ratios to toxin (Table 2). When combinatorial studies utilizing varying concentrations of LF10E or LF11H with a non-protective dose of anti-PA mAb W1 were performed, LF10E indicated a slight additive effect. Five of six animals were protected when nonprotective concentrations of LF10E (1:4 Ab:LF) and W1 (1:6 Ab:PA) were combined, but protection rapidly fell off at lower doses of either antibody (Table 4). Interestingly, mAb LF11H which exhibited far lower neutralizing ability in vitro, resulted in a robust synergistic protection when combined with subprotective doses of anti-PA mAb W1. This antibody, unable to protect at lower than equimolar ratios when used alone, was now able to protect at 1:4 (Ab:LF) submolar ratio when combined with mAb W1 at 1:10 (Ab:PA) (Table 5).

TABLE 4

Efficacy of LF10E and its combination with anti-PA W1 in protection of rat against lethal toxin challenge[a]

| Passive immunization | | Protection | | |
|---|---|---|---|---|
| MAbs/ antigen | Dose (Ab:toxin) | % | No. survival/ no. total | MTTD[b] (min) | P[d] |
| LF10E/LF | 1:2 | 100 | 6/6 | ND | 0.002 |
| | 1:3 | 67 | 4/6 | 136 | 0.061 |
| | 1:4 | 0 | 0/14 | 101 | |
| W1/PA | 1:5 | 33 | 2/6 | >140[c] | 0.455 |
| | 1:6 | 0 | 0/20 | 175 | |
| | 1:7 | 0 | 0/7 | 150 | |

TABLE 4-continued

Efficacy of LF10E and its combination with anti-PA W1
in protection of rat against lethal toxin challenge[a]

| Passive immunization | | Protection | | | |
|---|---|---|---|---|---|
| MAbs/ antigen | Dose (Ab:toxin) | % | No. survival/ no. total | MTTD[b] (min) | P[d] |
| LF10E + W1 | 1:4 + 1:6 | 83 | 5/6 | 266 | 0.015 |
| | 1:4 + 1:7 | 33 | 2/6 | 190 | 0.455 |
| | 1:5 + 1:6 | 33 | 2/6 | 249 | 0.455 |
| PBS | 0:1 | 0 | 0/22 | 82 | |

[a]Fischer F344 rat was injected i.v with 10 μg LeTx/rat with or without antibodies at various molar ratios of mAb:toxin and rats were monitored for minutes to death or survival.
[b]Mean time to death in minutes (MTTD) from 6 or more tested rats of each group was recorded. It was not available (NA) for groups with 100% protection.
[c]Three rats died at MTTD of 140 and one died overnight.
[d]Fisher's exact test (two-sided) was used to analyze the difference in protection between antibody-treated and nonantibody-treated (PBS) groups. A P value of <0.05 was considered as statistical significance. A total 6 animals for each group was used for the analysis

TABLE 5

Efficacy of LF11H and its combination with anti-PA W1
in protection of rat against lethal toxin challenge[a]

| Passive immunization | | Protection | | | |
|---|---|---|---|---|---|
| MAbs/ antigen | Dose (MAb:toxin) | % | No. survival/ no. total | MTTD[b] (min) | P[e] |
| LF11H/LF | 1:1 | 100 | 6/6 | NA | 0.002 |
| | 1:2 | 50 | 3/6 | >166[c] | 0.182 |
| | 1:3 | 0 | 0/8 | 172 | |
| | 1:4 | 0 | 0/6 | 126 | |
| W1/PA | 1:5 | 33 | 2/6 | >140[d] | 0.455 |
| | 1:6 | 0 | 0/20 | 175 | |
| | 1:7 | 0 | 0/7 | 150 | |
| LF11H + W1 | 1:3 + 1:6 | 100 | 6/6 | NA | 0.002 |
| | 1:3 + 1:7 | 100 | 6/6 | NA | 0.002 |
| | 1:3 + 1:10 | 83 | 5/6 | 371 | 0.015 |
| | 1:3 + 1:14 | 67 | 4/6 | 218 | 0.061 |
| | 1:4 + 1:7 | 100 | 6/6 | NA | 0.002 |
| | 1:4 + 1:10 | 100 | 6/6 | NA | 0.002 |
| PBS | 0:1 | 0 | 0/22 | 82 | |

[a]Fischer F344 rat was injected i.v with 10 μg LeTx/rat with or without antibodies at various molar ratios of mAb:toxin and rats were monitored for minutes to death or survival.
[b]Mean time to death in minutes (MTTD) from 6 or more tested rats of each group was recorded. It was not available (NA) for groups with 100% protection.
[c]One rat died in 166 minutes and two died overnight.
[d]Three rats died at MTTD of 140 and one died overnight.
[e]Fisher's exact test (two-sided) was used to analyze the difference in protection between antibody-treated and nonantibody-treated (PBS) groups. A P value of <0.05 was considered as statistical significance. A total 6 animals for each group was used for the analysis.

Figure 6A:
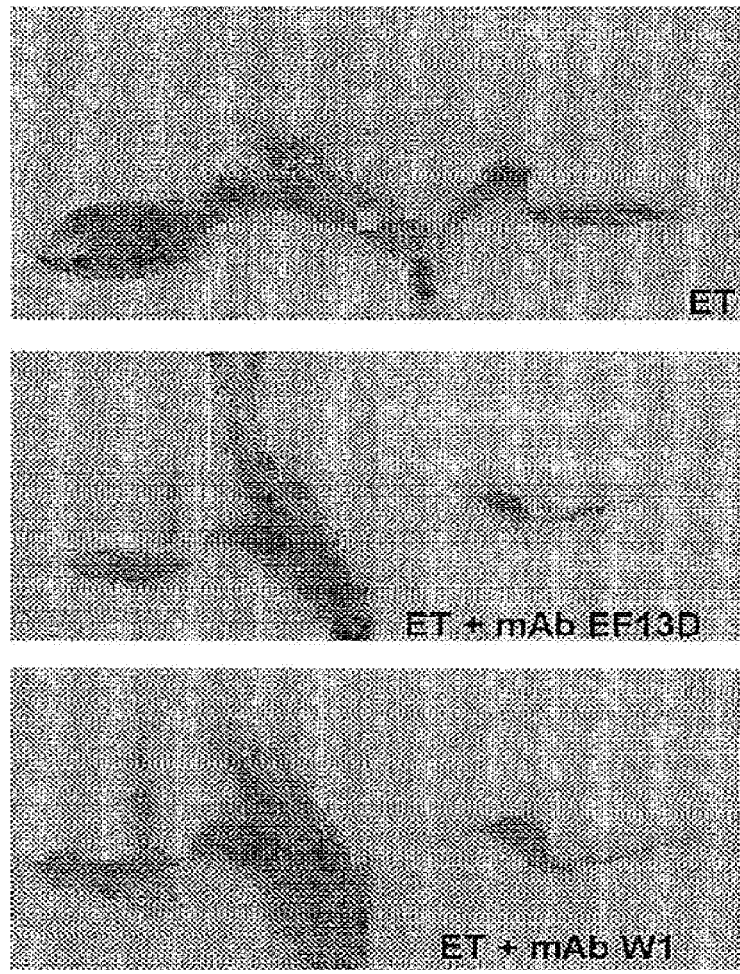
FIGS. 6A, 6B, 6C and 6D. Anti-EF mAb EF13D protects mice against ET-mediated footpad edema.
Figure 6B:
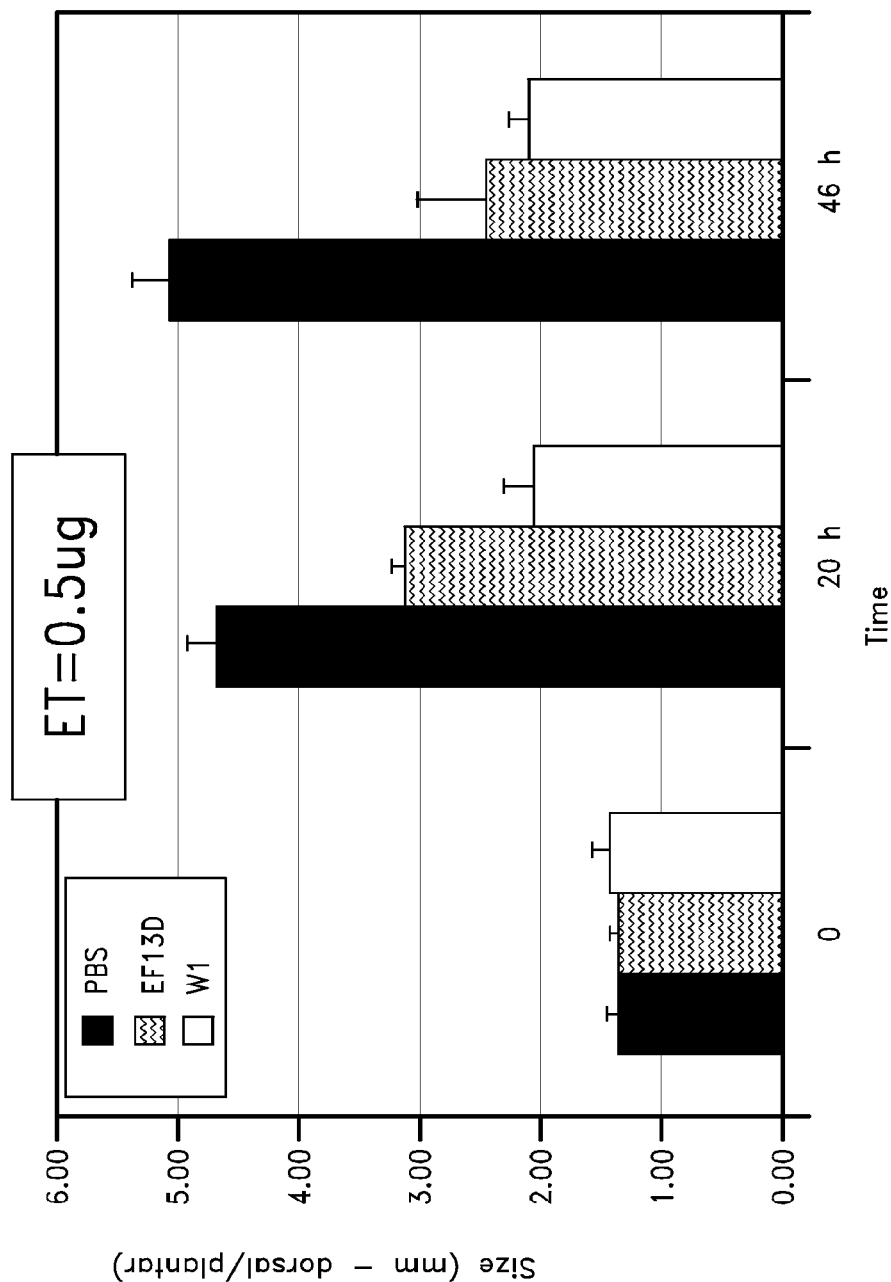
Figure 6C:
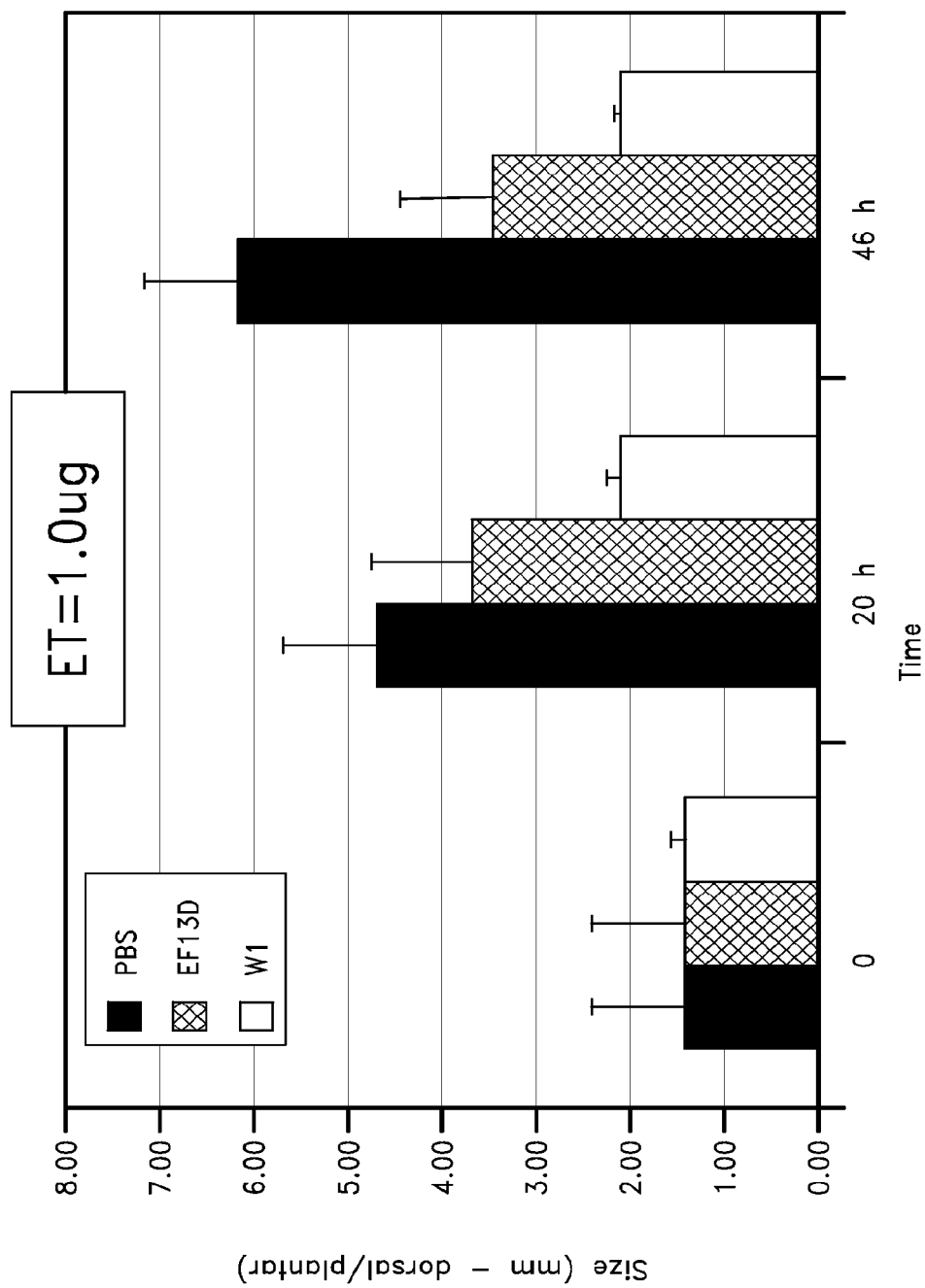
Figure 6D:
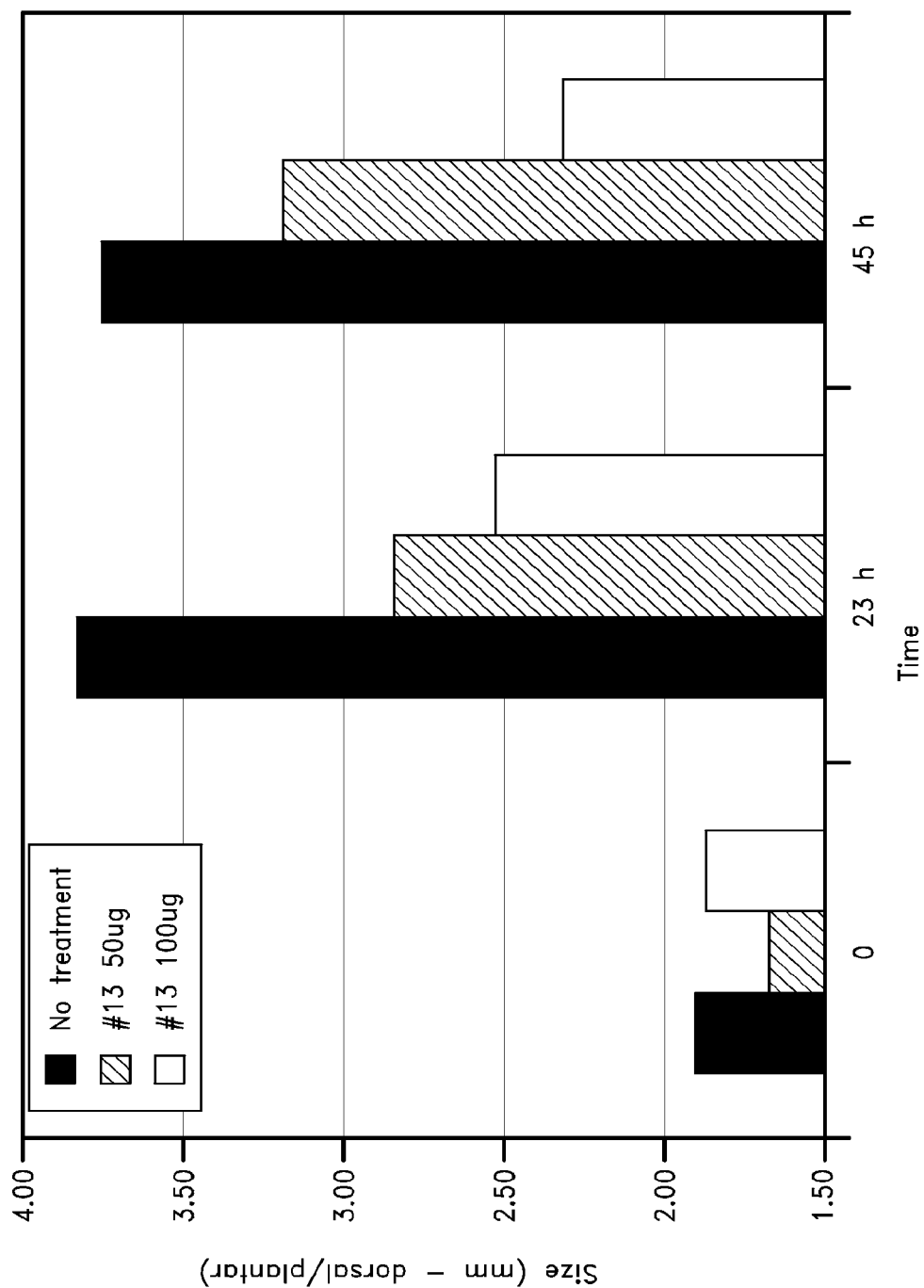

Anti-EF mAb EF13D Protects Mice Against ET-Mediated Footpad Edema and Lethality:

The in vivo efficacy of mAb EF13D was tested using two different models. The antibody was shown to significantly inhibit ET-mediated edema in the mouse footpad both when pre-mixed with toxin prior administration in the footpad (FIG. 6A-C) as well as when given systemically (IV) prior to toxin injection in footpads (FIG. 6D). The antibody was able to reduce ET-induced footpad size almost to the level of normal untreated or PBS-treated mice using three different doses of toxin (FIG. 6B-D).

Figure 7:
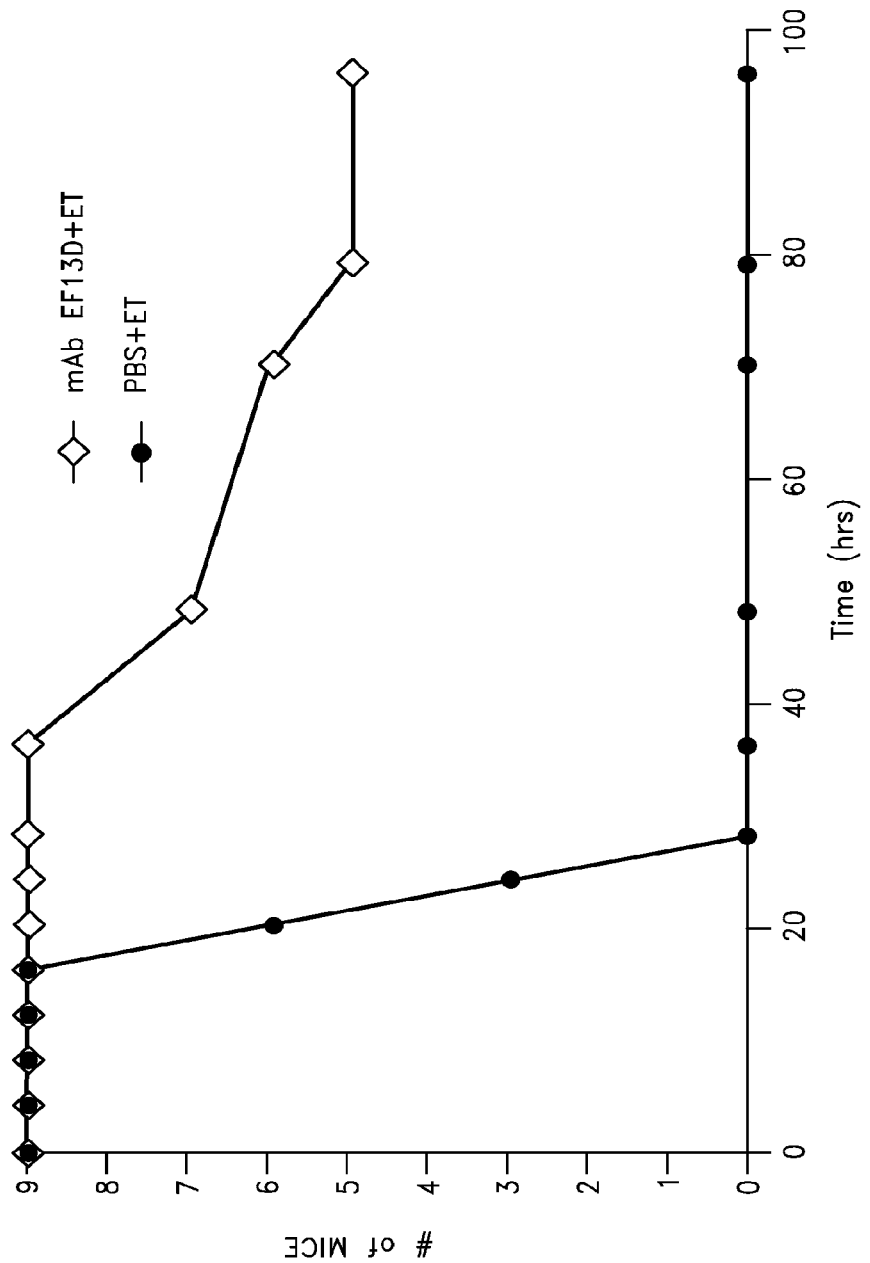
FIG. 7. Anti-EF mAb EF13D protects mice against ET-mediated lethality. C57BL/6J mice received a single mAb EF13D injection (50 ug, IV) 1 h prior to a lethal dose of ET (25 ug ET, IV) and survival was monitored for 100 h.

In other experiments, systemic pre-administration of mAb EF13D (50 ug/mouse) also provided significant protection against ET-mediated lethality in the mouse model (FIG. 7).

The example below describes in greater detail some of the materials and methods used in Example 1.

Example 2

Materials

The rabbit polyclonal antibodies to PA and LF were developed in our laboratory. This antibody cross reacts with EF and can be used for detection of either toxin by Western blot. MEK1 N-terminal (NT) antibody was purchased from Upstate Biotechnologies (Waltham, Mass.). Anti-PA monoclonal antibodies 14B7 and W1 have been previously described in detail (Chen, Z. et al. 2006 J. Infect. Dis. 193:625-633; Little, S. F. et al. 1988 Infect. Immun. 56:1807-1813) Infrared dye (IR-Dye)-conjugated secondary antibody (IRDye800CW IgG) used in Western blotting was purchased from Rockland Immunochemicals (Gilbertsville, Pa.).

Toxins:

PA and LF were made from Bacillus anthracis in our laboratory as previously described (Varughese, M. et al. 1998 *Mol. Med.* 4:87-95). EF, FP59 (a fusion of the N-terminus of LF (amino acids 1-254) and *Psuedomonas aueroginosa* Exotoxin A) and FP119 (a fusion of the N-terminus of EF (amino acids 1-260) and diphtheria toxin) were made from *Escherichia coli* as previously described (Arora, N. et al. 1994 *Infect. Immun.* 62:4955-4961).

For cytotoxicity or neutralization assays, toxin was prepared in Dulbecco's modified Eagle medium (DMEM) (Invitrogen, Carlsbad, Calif.) prior to addition to cells. Toxin for animal injections was prepared in sterile PBS with or without antibody. Concentrations and doses of LT refer to the amounts of each component (i.e. 100 ng LT/ml is 100 ng PA+100 ng LF/ml; 10 ug LT is 10 ug PA+10 ug LF).

Phage Library Construction and Selection.

The combinatorial cDNA library of chimpanzee r1/k antibody genes was constructed by cloning heavy and light chains at XhoI/SpeI and SacI/XbaI sites in pComb3H as described previously (Chen, Z. et al. 2006 *Proc. Natl. Acad. Sci. U.S.A* 103:1882-1887). The library was panned against recombinant EF immobilized on ELISA wells or LF protein immobilized on ELISA wells with blocking in solution with two previously isolated non-neutralizing anti-LF Fabs (Chen, Z. et al. 2006 *J. Infect. Dis.* 193:625-633). Panning was performed for three rounds and LF or EF-specific clones were selected by 96-well phage ELISA (Harrison, J. L. et al. 1996 *Methods Enzymol.* 267:83-109).

Fab and IgG Production and Purification.

Removal of phage coat protein III—encoding region from phagemid DNA by digestion with NheI/SpeI and re-ligation resulted in phagemid encoding soluble Fab. Fab was expressed and purified on a nickel-charged column as described (Chen, Z. et al. 2006 *Proc. Natl. Acad. Sci.* U. S. A 103:1882-1887). The conversion of Fab to IgG, the IgG expression and expression were carried out as described previously (Chen, Z. et al. 2006 *Proc. Natl. Acad. Sci.* U. S. A 103:1882-1887).

The purity of Fab and IgG were determined by sodium dodecyl sulfate polyacrylamide gel electrophoresis (NuPAGE MOP, Invitrogen, Carlsbad, Calif.). Protein concentrations were determined by both dye-binding assay (Pierce, Rockford, Ill.) and by measurement at OD280 assuming that 1.35 OD280 is equivalent to 1 mg/ml.

ELISA Analysis of Fab Specificity.

Recombinant EF or LF at 5 ug/ml and unrelated proteins (bovine serum albumin [BSA], thyroglobulin, lysozyme, and phosphorylase b) (Sigma, St. Louis Mo.) at 10 ug/ml in carbonate buffer (pH 9.5) were coated on ELISA microtiter plates. ELISAs were performed as previously described (Chen, Z. et al. 2006 *J. Infect. Dis.* 193:625-633).

Nucleic Acid Sequence Analysis of LF and EF-Specific Fab Clones.

The genes coding for the variable region of heavy (VH) and light (VL) chains of LF and EF-specific clones were sequenced, and their corresponding amino acid sequences were aligned. The presumed family usage and germ-line origin were determined for each VH and VL gene by search of V-Base, which is a compilation of all of the available human variable region IG germ line sequence (Cook, G. P. et al. 1995 *Immunol. Today* 16:237-242).

Affinity Measurement.

The kinetics analysis of the EF-neutralizing clone was performed in BIAcore 100 (GE healthcare, Piscataway, N.J.). The purified IgG was immobilized onto CMS chip using NHS/EDC coupling chemistry to achieve 500 RU. Two-fold serial dilutions of recombinant EF ranging from 200 nM to 0.78 nM were injected onto the chip surface. The kinetic interaction between EF and immobilized IgG was displayed in the sensorgram and evaluated by BIAevaluation software using 1:1 (Langmuir) binding model. For LF-neutralizing antibodies, kinetics analysis was performed in BIAcore 3000 (GE healthcare, Piscataway, N.J.). The LF was immobilized onto CM3 chip using NHS/EDC coupling chemistry to achieve 1420 RU. Anti-LF Fabs at concentrations ranging from 400 nM to 0.4 nM were injected onto the chip surface. The kinetic interaction between Fab and immobilized LF was displayed in the sensorgram and evaluated by globally modeling kinetic data as a continue distribution of affinity and rate constants (Svitel, J. et al. 2003 *Biophys. J.* 84:4062-4077).

LT Neutralization:

LT (100 ng/ml) was prepared in DMEM in a 96-well plate. Antibodies were diluted serially directly into the toxin mixture and incubated for 1 h at 37 C. Anti-PA antibody 14B7 was used on each plate as the control in all neutralization assays. The LT-mAb mixtures were then moved to RAW264.7 macrophage cells grown to 80-90% confluence in 96-well plates. Cells were incubated for 4 h and the cell viability was assessed by addition of MTT [3-(4, 5-dimethylthiazo-2-yl)-2,5-diphenyltetrazolium bromide] (Sigma, St. Louis, Mo.) at a final concentration of 0.5 mg/ml. Cells were then further incubated with MTT for 40 min, and the blue pigment produced by viable cells was dissolved by aspirating the medium and adding 50 µl/well of 0.5% (w/v) SDS, 25 mM HCl, in 90% (v/v) isopropanol and shaking the plates for 5 min prior to reading at 570 nm using a microplate reader. Results were plotted and the effective concentration for 50% neutralization (EC50) was calculated with Prism software (Graphpad Software Inc, San Diego, Calif.).

ET Neutralization:

Assays were performed as described for LT neutralization, except ET (100 ng/ml) was utilized, and cells were only incubated with toxin-antibody mixtures for 1 h prior to assessment of cAMP production levels using the BioTRAK cAMP enzyme immunoassay from Amersham Pharmacia Biotech (Piscataway, N.J.) according to manufacturer's protocol.

PA Binding, LF Binding and MEK Cleavage Assays:

LT was incubated with each mAb or PBS at 100-fold per weight excess for 1 h prior to addition to CHO (Chinese Hamster Ovary) cells or RAW264.7 cells in 6-well plates. Cells were treated with the toxin-antibody mixture at 37° C. for 1 h, medium was removed, cells were washed 5× in ice-cold PBS, lysed in RIPA buffer (1% Nonidet, 0.5% sodium deoxycholate, 0.1% SDS in PBS+COMPLETE protease inhibitor cocktail (Roche Applied Science, Indianapolis, Ind.)). Protein concentrations in lysates were quantified using the BCA assay (Pierce Biotechnology, Rockford, Ill.) for equal loading on gels. Western blot analysis was performed using anti-LF (1:1000), anti PA (1:5000) or anti-MEK1 NT (1:5000) antibodies. IR-dye conjugated secondary goat anti-rabbit IgG (1:20,000) were used for detection with the Odyssey Infrared Imaging System (LI-COR Biosciences, Lincoln, Nebr.).

Animal Studies:

Two Chimpanzees 1603 and 1609 were immunized with recombinant PA, LF and EF and the bone marrows were used for library construction as described previously (Chen, Z. et al. 2006 *J. Infect. Dis.* 193:625-633). Female Fischer 344 rats were purchased from Taconic Farms (Germantown, N.Y.) and used at 160-180 g. Female BALB/cJ or C57BL/6J mice were purchased from Jackson Labs (Bar Harbor, Me.) and used at 8-12 weeks of age. Fischer 344 rats (Female, 160-180 g) were injected via the tail vein with a mixture of antibody and PA+LF (LT), at different molar ratios (1:3-4, Ab:LT), prepared in sterile PBS or with LT alone. LT concentration was always held constant at 10 ug/rat and injection volumes were 200 µl/rat Animals were observed continuously for the first 8 h, then at 16 h and throughout the second day. Animals were monitored for signs of malaise and mortality. BALB/cJ mice were injected in one foot pad with ET (0.5 ug or 1.0 ug) pre-mixed with anti-EF mAb EF13D, anti-PA mAb W1 or PBS. Antibodies were used at 5 ug (10-fold or 20 fold per weight excess). Footpad injection volumes were 20 ul. Footpad edema was monitered at 20 h and 46 h after injection by measuring dorsal/plantar and medial/lateral sizes using digital calipers. In alternate experiments, mAb EF13D (50 ug or 100 ug/mouse) was pre-administered to mice systemically via intravenous injection 1 h prior to ET (0.25 ug) injection into footpads and footpad size was monitored. To test efficacy against ET lethality C57BL/6J mice received a single mAb EF13D injection (50 ug, IV) 1 h prior to administration of a lethal dose of ET (25 ug ET, IV) and survival was monitored for 100 h. All animal experiments were performed under protocols approved by the NIAID Animal Care and Use Committee.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A substantially pure polypeptide that binds a conformational epitope of anthrax edema factor (EF) antigen to which anti-anthrax EF13D monoclonal antibody binds, wherein said monoclonal antibody comprises a heavy chain CDR1 region having an amino acid sequence of SEQ ID NO:35, a heavy chain CDR2 region having an amino acid sequence of SEQ ID NO:37, a heavy chain CDR3 region having an amino acid sequence of SEQ ID NO:39, a light chain CDR1 region having an amino acid sequence of SEQ ID NO:43, a light chain CDR2 region having an amino acid sequence of SEQ ID NO:45, and a light chain CDR3 region having an amino acid sequence of SEQ ID NO:47, and wherein said substantially pure polypeptide is a variant of the anti-anthrax EF13D monoclonal antibody and said substantially pure polypeptide comprises:
  (a) a heavy chain amino acid sequence that is at least 95% identical to SEQ ID NO: 33 or a light chain amino acid sequence that is at least 95% identical to SEQ ID NO: 41; or
  (b) a conservative variation in the amino acid sequence of SEQ ID NO: 35, SEQ ID NO:37, SEQ ID NO:39, SEQ ID NO: 43, SEQ ID NO:45 or SEQ ID NO: 47.

2. The substantially pure polypeptide of claim 1, wherein said polypeptide comprises an amino acid sequence that is at least 95% identical to SEQ ID NO: 35, SEQ ID NO:37, SEQ ID NO:39, SEQ ID NO: 43, SEQ ID NO:45 or SEQ ID NO: 47.

3. A preparation comprising the substantially pure polypeptide of claim 2 and a pharmaceutically acceptable carrier.

4. A method for the diagnosis of anthrax disease comprising administering to a patient an effective amount of the preparation of claim 3, and detecting binding of the substantially pure polypeptide as a determination of the presence of anthrax disease.

5. A method of detecting the presence of anthrax EF in a biological sample comprising:
  contacting said sample with the preparation of claim 3; and
  assaying binding of the substantially pure polypeptide as a determination of the presence of said anthrax EF.

6. The substantially pure polypeptide of claim 1, wherein said polypeptide comprises a conservative variation in the amino acid sequence of SEQ ID NO: 35, SEQ ID NO:37, SEQ ID NO:39, SEQ ID NO: 43, SEQ ID NO:45 or SEQ ID NO: 47.

7. A preparation comprising the substantially pure polypeptide of claim 6 and a pharmaceutically acceptable carrier.

8. A method for the diagnosis of anthrax disease comprising:
  administering to a patient an effective amount of the preparation of claim 7, wherein said substantially pure polypeptide is attached to a detectable label to form a labeled substantially pure polypeptide; and
  detecting binding of the labeled substantially pure polypeptide to anthrax EF as a determination of the presence of anthrax disease.

9. A method of detecting the presence of anthrax EF in a biological sample comprising:
  contacting said sample with the preparation of claim 7; and
  assaying binding of the substantially pure polypeptide as a determination of the presence of said anthrax EF.

* * * * *